(12) United States Patent
Mahiout

(10) Patent No.: US 6,492,336 B1
(45) Date of Patent: Dec. 10, 2002

(54) PERITONEAL DIALYSIS FLUID

(75) Inventor: Arezki Mahiout, Hanover (DE)

(73) Assignee: Allied Therapeutics Limited, London (GB)

( * ) Notice: Subject to any disclaimer, the term of this patent is extended or adjusted under 35 U.S.C. 154(b) by 0 days.

(21) Appl. No.: 09/463,758

(22) PCT Filed: Jul. 3, 1998

(86) PCT No.: PCT/GB98/01960
§ 371 (c)(1),
(2), (4) Date: Jun. 8, 2000

(87) PCT Pub. No.: WO99/01144
PCT Pub. Date: Jan. 14, 1999

(30) Foreign Application Priority Data

Jul. 4, 1997 (GB) .............................................. 9714218

(51) Int. Cl.⁷ .................... A61K 33/14; A61K 31/70; A61M 1/28
(52) U.S. Cl. .......................................... 514/25; 514/24
(58) Field of Search ..................... 514/24, 25

(56) References Cited

U.S. PATENT DOCUMENTS

| 4,879,280 A | 11/1989 | Seyffart et al. ............... 514/53 |
| 6,077,836 A | 6/2000 | Milner ......................... 514/54 |

FOREIGN PATENT DOCUMENTS

JP   8-131541   *   5/1996

OTHER PUBLICATIONS

Derwent Abstract, Accession No. 1996–304198, abstracting JP 8–131541, 1996.*
Luke, Robert C., "Dialysis": in Wyngaarden et al., Cecil Textbook of Medicine, W.B. Saunders Co., Philadelphia, pp. 541–545, 1992.*
International Search Report of PCT/GB98/01960, mailed Mar. 11, 1998.

* cited by examiner

*Primary Examiner*—John Pak
(74) *Attorney, Agent, or Firm*—Sterne, Kessler, Goldstein & Fox, p.l.l.c.

(57) ABSTRACT

Peritoneal dialysis fluids and the use thereof for performing peritoneal dialysis are disclosed. The peritoneal dialysis fluid comprises a physiologically acceptable aqueous solution containing physiologically acceptable inorganic anions and cations and, as an osmotic agent, at least one sugar derivative, at concentrations sufficient for the removal of water and solutes from a patient by peritoneal dialysis. The sugar derivative is a compound of formula

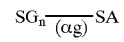

wherein each SG, which may be the same or different, represents a residue of a physiologically acceptable metabolizable sugar, SA represents a residue of a physiologically acceptable metabolizable sugar alcohol, n is from 1 to 4 and $$\overline{(\alpha g)}$$

represents a glycoside linkage which is cleavable by an α-glycosidase enzyme.

22 Claims, 15 Drawing Sheets

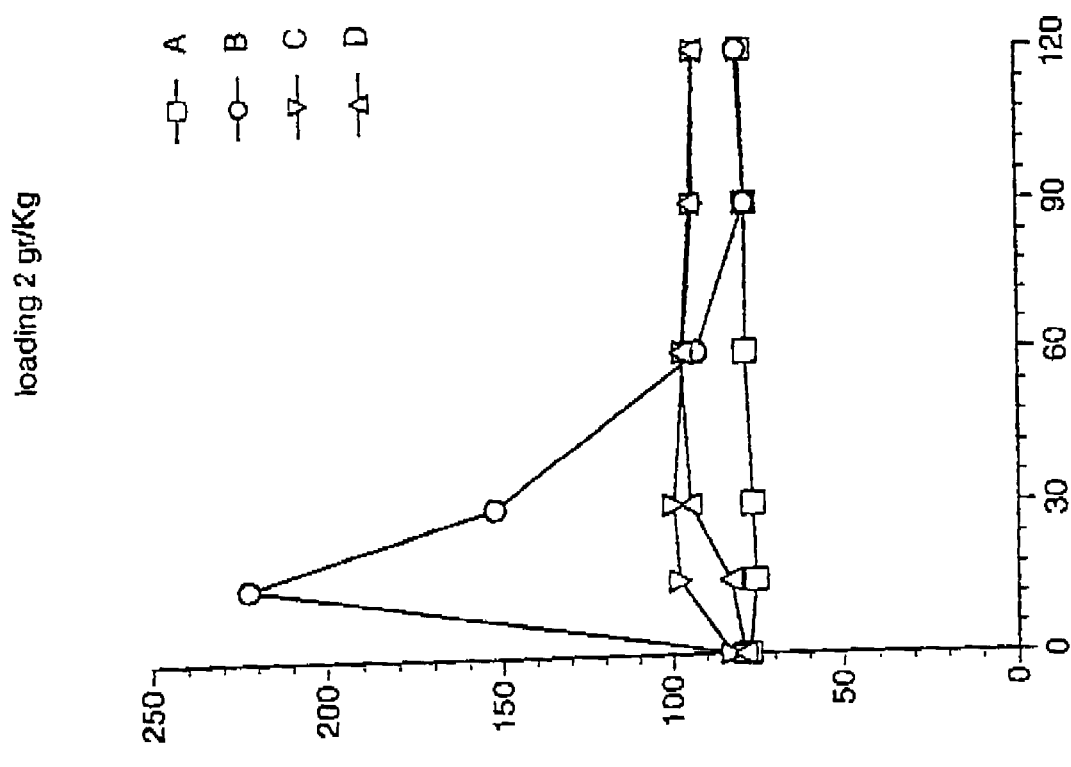
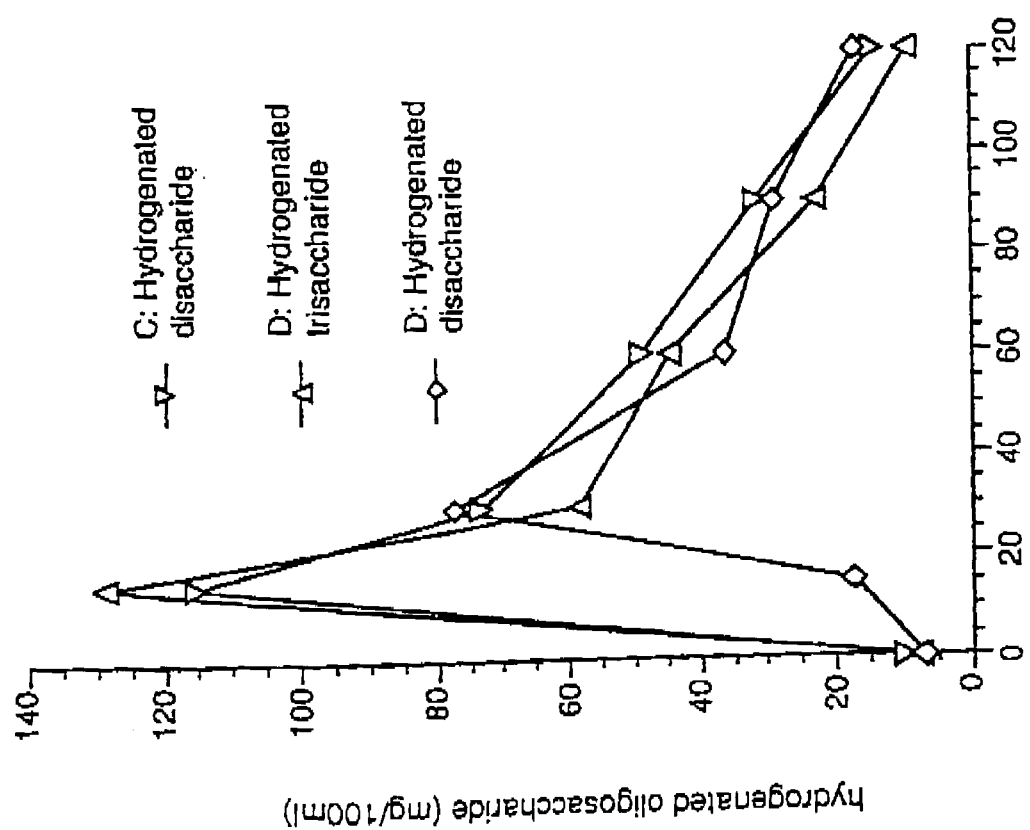

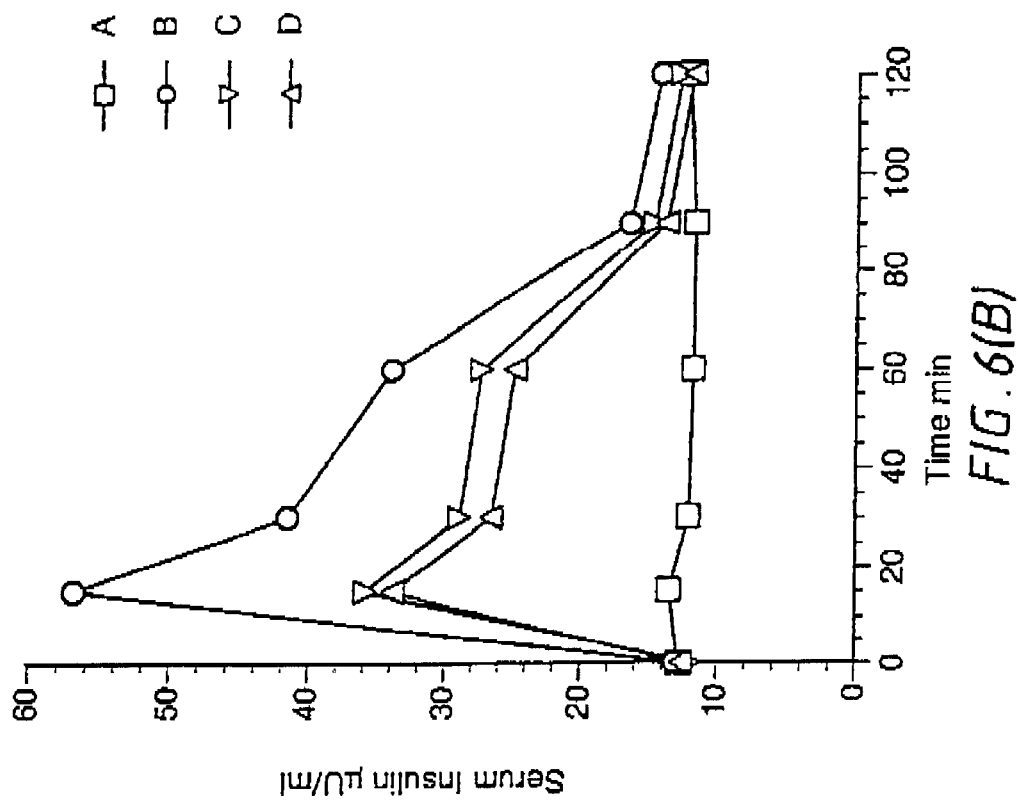
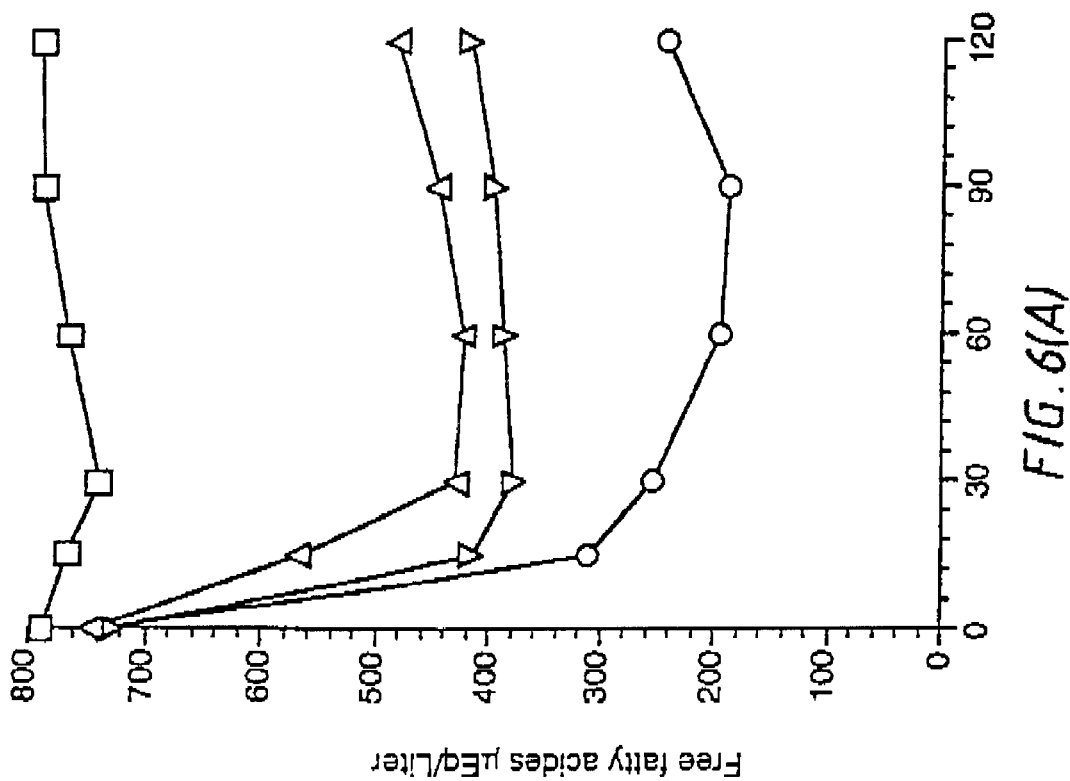
FIG. 6(B)
FIG. 6(A)

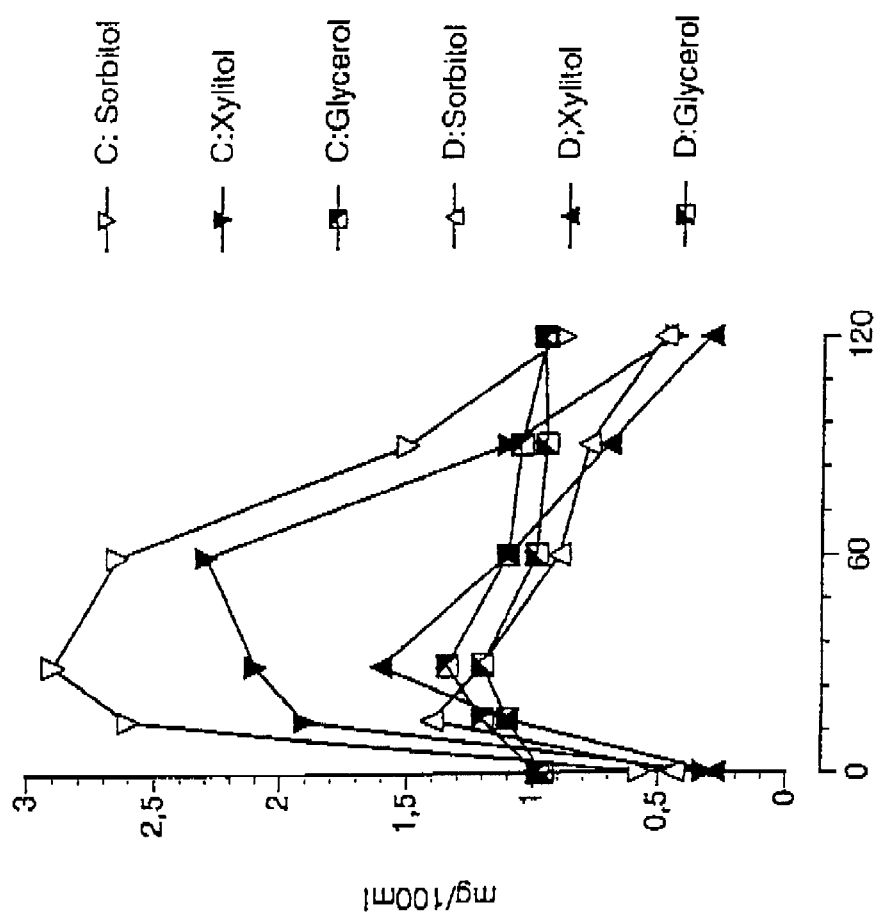
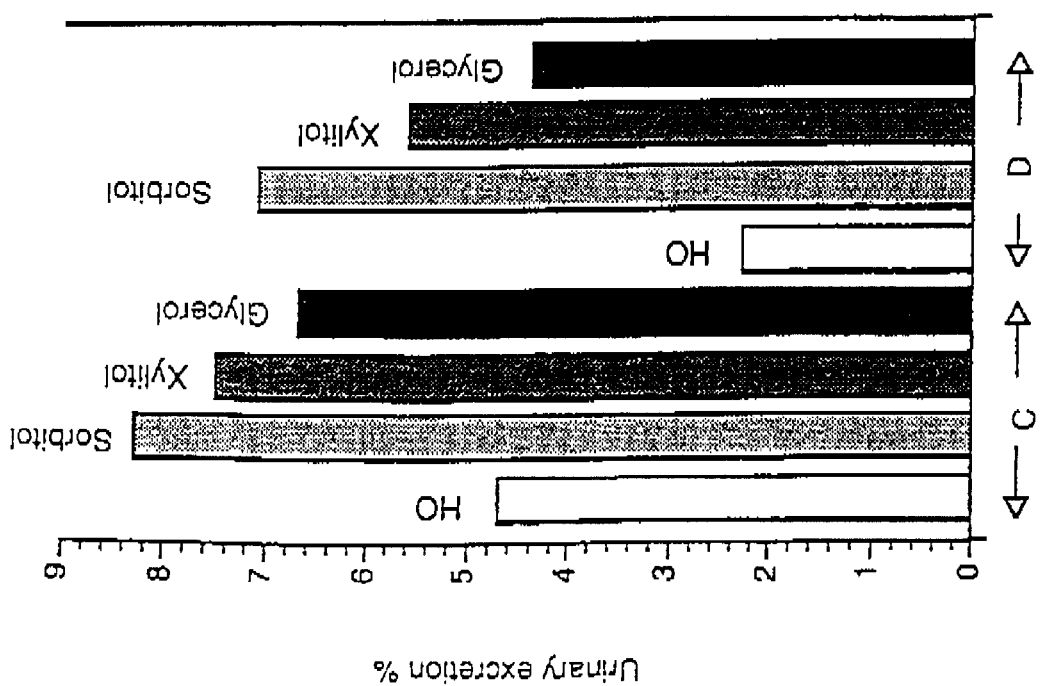
FIG. 7(A)
FIG. 7(B)

FIG. 8

| | Control 4,25% Glucose/Bicarbonate 35 mmol/L; pH=7,4 | Glucose 4,25%/bicarbonate 30 mmol/L; Pyruvate 10 mmol/L; pH=7,4 | 4% Hydrogenated disaccharide/Bicarbonate 35 mmol/L; pH=7,4 | 4% Hydrogenated disaccharide/ Pyruvate 10 mmol/L; Bicarboante 30 mmol/L; 7,4 |
|---|---|---|---|---|
| PBMC (O2-)/ mmol/106 Cells/min | 1,98± 0,32 | 1,12 ± 0,2 | 1,82 ± 0,32 | 1,94±0,2 | 1,98±0,24 |
| PBMC (IL-1β) ng/ml | 7,3±1,7 | 4,12 ± 0,7 | 6,1 ± 2,8 | 7,4±1,4 | 7,2±1,6 |

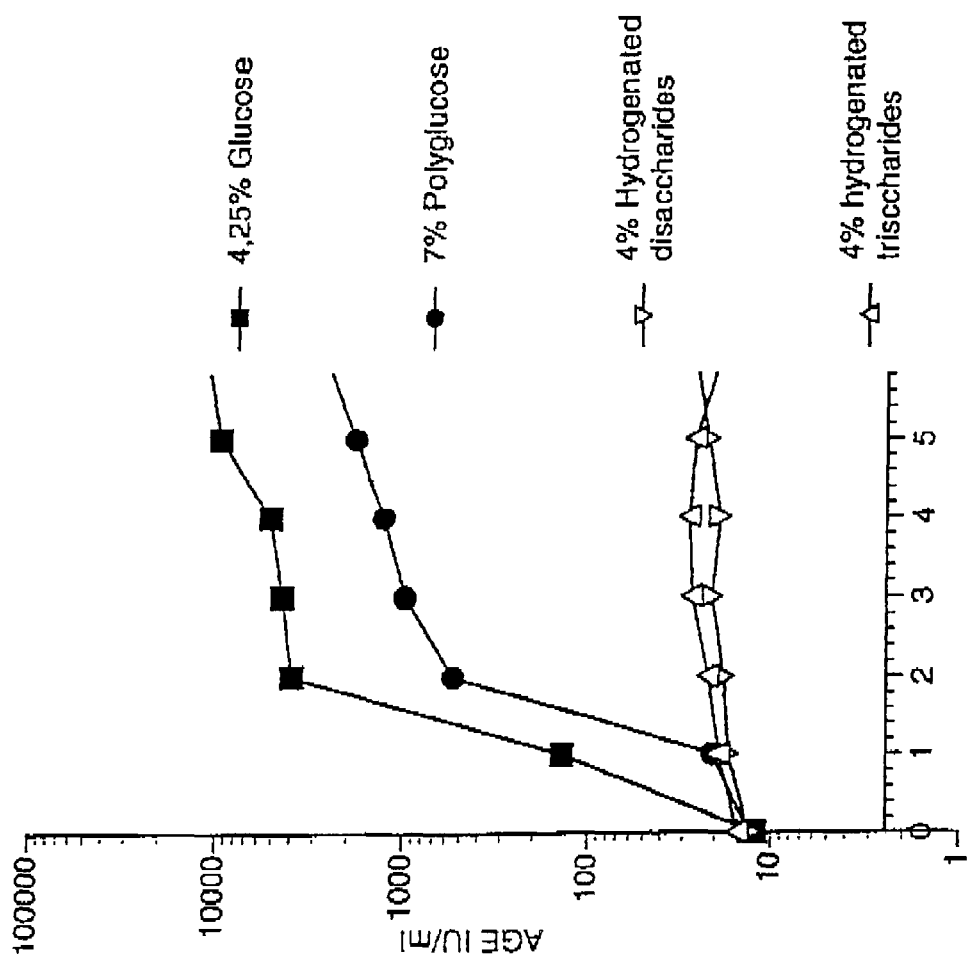
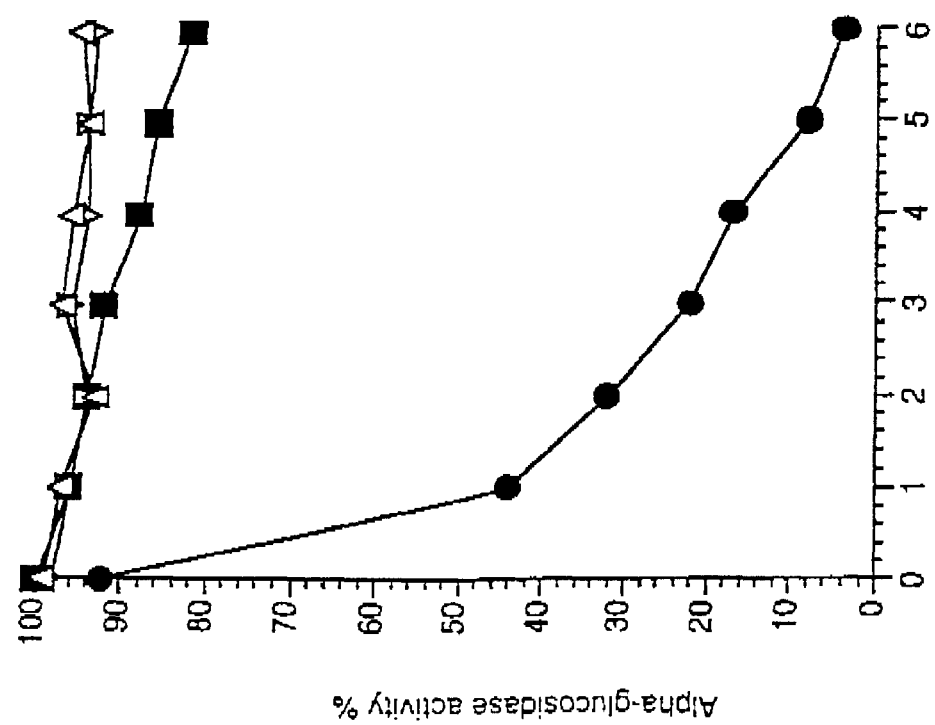
FIG. 9(A)
FIG. 9(B)

(GP)$_1$ SORBITOL ; MW=344

REDUCTION OF THE CARBONYL GROUP (GP)$_1$ XYLITOL ; MW=312

GLUCOSYL UNIT

XYLITOL

REDUCTION OF THE CARBONYL GROUP (GP)$_1$ GLYCEROL ; MW=252

REDUCTION OF THE CARBONYL GROUP (GP)$_2$SORBITOL ; MW= 502

[GP]₂XYLITOL; MW=472

REDUCTION OF THE CARBONYL GROUP (GP)₂ GLYCEROL ; MW=412

PERITONEAL DIALYSIS FLUID

This application is a 371 of PCT/GB98/01960, filed Jul. 3, 1998.

The present invention relates to novel peritoneal dialysis fluids and to the use thereof for performing peritoneal dialysis.

BACKGROUND TO THE INVENTION

In the human body, the transfer of solutes and toxins from one body fluid compartment to another occurs by a variety of chemical and physical processes which include diffusion, osmosis and active transport. In this respect, toxins, excess of water and solutes are transferred from the tissues to the blood stream and then via the arteries to the kidneys. In the kidneys substances to be eliminated may be metabolised and eliminated in the urine.

In renal disease, kidney function is not sufficient to maintain an adequate degree of clearance, thus the accumulation of water and uremic toxins occurs in the body. Today, the medical treatments available for patients suffering from a malfunction of the kidney are kidney transplantation, extracorporeal hemodialysis, or alternatively intracorporeal peritoneal dialysis. Treatment by kidney transplantation. remains the preferred therapy as the patients may lead a near normal life. Hemodialysis (an extracorporeal procedure) and peritoneal dialysis (an intracorporeal procedure) are the alternative therapies to treat end stage renal disease (ESRD) patients.

Peritoneal dialysis is a well established intracorporeal procedure which is used today as an alternative to the extracorporeal hemodislysis. In fact, in many instances, peritoneal dialysis is preferred to the extracorporeal therapy.

However, in some medical centers, hemodialysis technology is not available and the cost of peritoneal dialysis in general may be lower when other medical complementary care procedures are excluded, For some patients, the surgery required to prepare for permanent blood access has been unsuccessful. Finally, some nephrologist prefer peritoneal dialysis as a hemodialysis procedure, because it uses a natural membrane and residual (resting) kidney function may be maintained for a long period after starting the therapy.

In peritoneal dialysis, a dialysis fluid is introduced with the aid of a catheter into the peritoneal cavity in the abdomen of the patient. This catheter is permanently implanted by surgery through the abdominal wall. The peritoneal cavity is flooded with the dialysis fluid, left for an appropriate lapse of time, and then drained.

Peritoneal dialysis relies on the physiological activity of the peritoneum. The peritoneum is a layer of mesothelial cells which contains large numbers of blood vessels and capillaries. These facilitate use of the peritoneal cavity as a semipermeable membrane. The peritoneal dialysis procedure involves the introduction of a fluid into the peritoneal cavity for a suitable period of residence time. This allows an exchange of solutes between the dialysate and the blood during the residence time of the dialysate in the peritoneum. This residence time (also called dwell time) varies from patient to patient and can be about five hours. Accordingly, the frequency with which the dialysate has to be exchanged is on average, four to five times per day.

The removal of uremic toxins takes place across the peritoneal membrane by diffusion, and excess water in the body is removed by an osmotic pressure induced by an osmotic agent such as glucose. Glucose is currently the standard osmotic agent and is generally used in a concentration in the dialysis fluid (% weight by volume) of from 1.36 to 4.25.

As indicated, glucose is currently included in the dialysis fluid to impart the necessary osmotic gradient, i.e., it is the standard osmotic agent for dialysis solutions. However, because it is introduced into the peritoneal cavity, it will find its way into the bloodstream during therapy. In fact, glucose crosses the peritoneum so rapidly that the magnitude of the osmotic gradient falls within 2–3 hours after the injection of the dialysate. This causes the unwanted result of water being reabsorbed from the dialysate toward the end of the dialysis period, i.e. before the dialysis fluid is replaced with fresh fluid.

Further, the amount of glucose which is absorbed represent a large portion of the patient's energy uptake, possibly being as high as 15–40%. The clinical consequences are hypoglycemia and obesity. In addition, the sugar has a long term undesirable effects, especially for diabetic patients, for whom there is an additional requirement to increase the injection of the insulin doses or to introduce additional insulin in the dialysis fluid.

A further negative effect of using glucose is the formation of advanced glycation of proteins in diabetic and uremic patients, due to a high concentration of glucose, which is not quickly metabolized. This disadvantage may be the cause of peritoneal membrane damage during therapy and may be also responsible for membrane scelerosis which decreases the salt clearance.

The reduction of advanced glycated end product (AGE) uremia in the peritoneal membrane is today a new considerable factor in assessing the performance of dialysis therapy[1]. Glycation of the protein matrix of the peritoneum membrane has been demonstrated in CAPD patients. The local biological effects of AGE on peritoneal cells, has been demonstrated in vitro and involves activation of mesotheial cells and the pathological change of the peritoneal cell matrix which may cause scelorosis.

One of the most important and difficult aspects of peritoneal dialysis, is finding a suitable osmotic agent for the preparation of the dialysate, by which the required osmotic pressure can be achieved without the secondary problems referred to above. An appropriate osmotic agent should have the following properties: it should satisfy the needs for peritoneal dialysis; be a non-toxic substance: the accumulation of unacceptable derivatives or metabolites in the peritoneum or in the circulation should be avoided; it should not rapidly cross the peritoneal membrane into the blood and in this respect it should allow maintenance of the required ultrafiltration; it should not react with the peritoneum or with proteins, leading to secondary reactions involving pathology of the peritoneal membrane, of peritoneal cells, or of cells from the circulation; it should not alter cell function which can reduce natural local phagocytosis, and the ability of the immune system to kill bacteria.

To date, several osmotic agents such as dextran[2], fructose[3], xylitol[4], sorbitol[5], polyglucose[7,8], amino acids[9], glycerol[10], peptides[11], and plasma substitutes[12], have been proposed, but most of these have not completely satisfied the medical needs.

In Dolkart R. E WO 82/03987, the use of a monosaccharide sugar alcohol such as glycerol has been suggested as an alternative osmotic agent to overcome glucose overloading, mainly in diabetic patients. In addition, xylitol and sorbitol have also been proposed in the 1970's. However when given in their pure form and in an amount sufficient to exert transperitoneal ultrafiltration, all these sugar alcohols have a high transperitoneal absorption and lead to their accumulation in the blood at a rate over the rate of their metabolic clearance, thus causing several adverse reactions.

In U.S. Pat. No. 3,911,915 by Seifter et al, a disaccharide in the form of maltose has been proposed for intraperitoneal use. Although maltose has been demonstrated to have beneficial effects following intravenous administration[14] in respect to the insulin need and glucose overloading when compared to glucose, this substance was not provided a suitable osmotic agent in peritoneal dialysis.

The use of high molecular weight polyglucose have been proposed by Milner in the U.S Pat. No. 3,928,135 for the use as ingredients for oral or intravenous administration, and by Alexander in No. WO 83/00087 for the special use as osmotic agent in peritoneal dialysis. This proposal by Alexander is based on the concept that an iso-osmotic solution containing polyglucose exercises transperitoneal ultrafiltration. Although glucose polymers seem to be well tolerable by patients, plasma oligosaccharide concentrations sharply and chronically increased. Long term effects of these levels are not yet known. In this respect, long term effects resulting in storage disease with problems of the reticulo-endothelial system blockade as known for large molecular weight plasma substitutes[13] are speculated. On the other hand, the effects of accumulation and circulation of large molecular weight oligosaccharide may increase the levels of complex Amadori and Mallard products, These include glycated end products. A particular undesirable effect is that the Amadori products formed from polyglucose (the early and reversible stage of glycation) have a strong inhibitory effect on the activity of the α-glucosidase enzyme which is responsible for the metabolism of oligosaccharide.

SUMMARY OF THE INVENTION

According to an aspect of the present invention there is provided a dialysis fluid, said fluid comprising a physiologically acceptable aqueous solution containing physiologically acceptable inorganic anions and cations and as an osmotic agent, at least one sugar derivative, said physiologically acceptable inorganic anions and cations and said at least one sugar derivative being present in concentrations sufficient for the removal of water and solutes from a patient by peritoneal dialysis, characterized in that the sugar derivative is a compound of formula

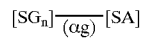

wherein the or each SG, which maybe the same or different, represents a residue of a physiologically acceptably metabolizable sugar, SA represents a residue of a physiologically acceptable metabolizable sugar alcohol, n is from 1 to 4 and $$\overline{(\alpha g)}$$

represents a glycoside linkage that is capable of being cleaved by an α-glycosidase enzyme. Preferably, n is 1 or 2. However, as indicated, n may also be 3 or 4.

Preferably, the adduct of formula

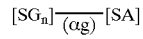

is a hydrogenated oligosaccharide (especially a hydrogenated α-D-oligosaccharide). Especially preferred are such compounds wherein the or each SG is a glucose residue.

Where the term "hydrogenated oligosaccharide" is used herein to refer to a compound of Formula

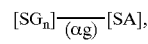

such usage does not necessarily mean that the substance in question has been prepared or manufactured by hydrogenation of an oligosaccharide starting material, although such a method of preparation is possible. Thus the adducts of formula

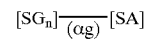

may be prepared by chemical or enzymatic procedures in which the residues of formulae [SG] and [SA] are linked together, or different [SG] and [SA] residues are exchanged for one another.

Where hydrogenation procedures are used, a compound of formula

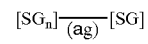

may be hydrogenated to form a compound of formula

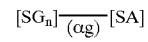

Similarly, the term "sugar alcohol" as used herein, is used interchangeably with the term "polyol" to refer to residues obtainable by hydrogenating sugar residues.

So far as the inventor of this invention is aware, hydrogenated oligosaccharides have not been suggested hitherto for intravenous or intraperitoneal perfusion. Specific hydrogenated oligosaccharide have however been the subject of studies as oral ingredients in respect to their digestion and absorption in the intestinal tract and are believed to be non-toxic and safe to use.

Thus the extent to which oligosaccharides can be modified in order to create a more suitable substance than glucose has hitherto been studied only with the objective of reducing caries, reducing the need for insulin in diabetic patients, and for reducing energy uptake, and as sweeteners for oral ingestion. Methods applied for making such compounds include transglycosidation, to form the desirable (1→6) and (1→4) glucosyl linkage and chemical reduction of a carbonyl group into the corresponding polyol moiety. Thus, the so-called Palatinit®, an equimolar mixture of alpha-D-glucopyranosido-1,6-sorbitol and alpha-D-glucopyranosido-1,6-mannitol has been prepared by microbial transglycosidation, followed by chemical reduction. The terms "oligosaccharide alcohol" or "hydrogenated oligosaccharide" have been proposed by Grupp et al. in describing Palatinit as a hydrogenated palatinose[15]. Known oligosaccharides having polyol moieties have also been synthesized by Ducan et al[18], Sawai & Hehre[19], Lindberg[20], Fischer and Seyferth[21].

The invention in its more specific aspects relates to the application of hydrogenated α-D-oligosaccharides as new osmotic agents in peritoneal dialysate, specifically, such compounds having α-D-glucosyl arrangement with (1→6) or a (1→4) glucosyl linkages in which the non-reducing sugar at the end of the glucosyl arrangement has been hydrogenated. The hydrogenated alpha-D-oligosaccharides used according to the invention include, but are not limited to those which can be isolated as a naturally existing entity, or can synthetically be derived by known chemical or enzymic reactions from available natural carbohydrate substrates. The oligosaccharides used in this invention, desirably result from the modification of natural carbohydrates by transglycosidation, e.g. replacement of constitutent monosaccharide(s) by different building blocks (saccharide units), and chemical reduction of carbonyl groups into a corresponding polyol moiety.

The resulting preferred hydrogenated alpha-D-oligosaccharides can be used in a homogeneous form or as mixtures and desirably contain between one or two glucosyl units plus one terminal polyol (i.e. a unit at the end of the glucosyl chain).

The invention thus in its preferred aspects relates the use of modified oligosaccharides, more particularly hydrogenated alpha-D-oligosaccharides with specifically (1→6) or a (1→4) glucosyl linkages (also called oligosaccharide alcohols) to replace glucose monohydrate or glucose polymers in peritoneal dialysis. Such hydrogenated alpha-D-oligosaccharides can be designed to be well tolerated and metabolized in uremic patients. The use in formulations of such hydrogenated alpha-D-oligosaccharide can result in low levels of transperitoneal absorption, biocompatibility in terms of cell function and effect on the peritoneal matrix, an effective osmotic effect of longer duration (dwell time), and the reduction of the requirement for insulin in diabetic patient.

Preferred aspects of the invention are based upon specific choices of the glucosyl arrangement of the oligosaccharide alcohol, upon the number of glucosyl groups, on the identities of the terminal polyols (sugar alcohols), and on the proportion in the mixture of different polyols.

In carrying out the invention, the manufacture of the preferred hydrogenated alpha-D-oligosaccharide may be based on (i) transglycosidation to form (1→6) and (1→4) glycoside linkages and replacement of constituent monosaccharides by a different building blocks, or (ii) chemical reduction of the last sugar of a disaccharides and/or trisaccharide.

In accordance with preferred aspects of this invention, the hydrogenated oligosaccharide with specifically (1→6) or a (1→4) glucosyl linkages are used to make dialysis solutions.

Most preferably the dialysis solutions are aqueous solutions with a pH between 5.4 and 7.4, and preferably in the physiological range of from pH 7.0 to 7.4.

The solutions of this invention may contain typical physiological inorganic salts which are commonly used in peritoneal dialysate solution, e.g. sources of $Na^+$, $K^+$, $Ca^+$ and $Cl^-$ ions, Buffers to be use in the solution to achieve the correction of the metabolic acidosis can include lactate, bicarbonate, pyruvate or a combination of pyruvate and bicarbonate.

The proportion of the hydrogenated oligosaccharide can vary, but normally would be in the range of about 1 to 60% by weight of the dialysate solution. The hydrogenated oligosaccharide may thus be added to a water solution containing typically from 116 to 140 mEq/liter of sodium, 0 to 5 mEq/liter of calcium, 100 to 144 mEq/liter of chloride, and 5 to 40 mEq/liter of bicarbonate and/or pyruvate and/or lactate.

Preferred hydrogenated alpha-D-oligosaccharide of the invention are ones possessing one and/or two glucosyl units plus a non-reducing terminal sugar alcohol or polyol unit. These sugar alcohols or polyols are preferably ones which are readily metabolized in humans. Examples include glucytol (sorbitol ), xylitol, ribitol, and glycerol.

Preferably, oligasaccharide alcohols with the defined specified terminal sugar alcohols or polyols, are mixed in proportions to ensure that the respective end metabolites remain below the metabolic capacity of the (usually uremic) patients being treated. The oligosaccharide alcohol used in the invention include those which can be isolated as a naturally existing entities, or ones which can synthetically be derived using known chemical or enzymic reactions from available natural carbohydrate substrates.

In accordance with a further preferred aspect of this invention, hydrogenated disaccharides with a molecular weight of from 254 to 368 MW can be used as a complete or as a partial substitute for glucose. However, a mixture of hydrogenated alpha-D-oligosaccharide obtained by chemical reduction of a carbonyl group into different polyols moiety is preferred. The use of hydrogenated disaccharide is preferred, while it represents the most economical and realistic way of producing hydrogenated disaccharide which is metabolised through the action of alpha-glucosidase, without risk for the patients.

The hydrogenated alpha-D-oligosaccharide most suitable and applicable for peritoneal dialysis are the O-alpha-D-glucopyranosido-1,6-sorbitol (GPSorbitol), O-alpha-D-glucopyranosido-1,4-D-Xylitol(GPXylitol), O-alpha-D-glucopyranosido-1,6-ribitol (GPRibitol), O-alpha-D-glucopyranosido-1,6-glycerol (GPGlycerol). These contain respectively terminal sorbitol, xylitol, ribitol, and glycerol residues attached to a single glucose residue, In accordance with the invention, the proportions of the various oligosuccharide components may be adjusted to take account of the fact that part of the ofigosaccharide alcohol which enter the blood circulation by transperitoneal absorption, should be rapidly metabolized to prevent blood hyperosmolality. For instance GPSorbitol, GPXylitol, GPRibitol and GPGlycerol are rapidly metabolized and can be included at a relatively high concentration. On the other hand, hydrogenated alpha-D-oligosaccharide involving terminal mannitol, arabitol, and dulcitol residues, desirably should be absent or included at very low proportion, (preferably smaller as 1%) because they are metabolized more slowly.

Preferably, disaccharide hydrogenated alpha-D-oligosaccharide mixtures are used. Optimal formulations comprise mixtures of GPSorbitol, GPXylitol, GPGlycerol and GPRibitol. These may be present in approximately equal amounts, i.e. a mixture of 25% of each.

Alternatively, a mixture of hydrogenated alpha-D-oligosaccharides derived from disaccharides and trisaccharides with a molecular weight from 256 MW to 524 MW can be used as complete or as partial substitute for glucose. These may be based on the conversion of natural carbohydrates substrates such as standard partial hydrolysates of maize starch, to hydrogenated oligosaccharides. The proportion in the resulting mixture of hydrogenated oligosaccharides of disaccharides and trisaccharide may vary between 1% and 99%. The hydrogenated alpha-D-oligosaccharide more suitable and applicable for peritoneal dialysis are similar to those prescribed in the disaccharide form, except that the average number of the glucosyl residues lies between one and two.

Alternatively a preparation of hydrogenated trisaccharide of homogeneous molecular weight can be used as a complete or as partial substitute for glucose. In accordance with the invention, the use of the 524 Molecular Weight hydrogenated trisaccharide may have the advantages that the transperitoneal absorption is less than the hydrogenated oligosaccharide in a disaccharide form, and after hydrolysis in the circulation there are less polyols generated. Therefore, the osmolality and metabolic half life is relatively reduced compared to the disaccharide form.

The naturally existing natural carbohydrate substrates, which may be involved in the preparation of hydrogenated alpha-D-oligosaccharides useful in the present invention may comprise the products of standard partial hydrolysis of maize starch. These typically contain 11% of maltose and 9.1% of trisaccharide. The most conveniently prepared hydrogenated alpha-D-oligosaccharide is the alpha-D-glucopyranosido-1,6-sorbitol, which may be obtained by microbial Protamino-bacter rubrum transglycosidation of saccharose into alpha-glucopyranosido-1,6-fructose (palatinose or isomaltulose), followed by chemical reduction of palatinose into the mixture GPSorbitol and GPMannitol[16]. The isomeric disaccharide alcohols can be fractionated by fractional crystallization from aqueous solution[17]. Using the same principles, other hydrogenated alpha-D-oligosaccharides such as O-alpha-D-glucopyranosido-1,4D-xylitol[18], Oalpha-D-glucopyranosido-1,6-glycerol[19] can also be manufactured. Higher molecular weight hydrogenated trisaccharides with (1→6) or (1→4) glucosyl linkages[20,21] can also be prepared in the same way.

Preferably, up to 60 grams of hydrogenated oligosaccharide in disaccharide or trisaccharide form may be present per liter of peritoneal dialysis solution. This range of concentrations can be used for all formulations irrespective of the molecular weight of the hydrogenated oligosaccharide and irrespective of what mixtures are used.

In the formulation of dialysis solutions based on hydrogenated disaccharides which comprise a homogeneous or equimolar mixtures of GPSorbitol, GPXylitol, GPRibitol, and GPGlycerol with the molecular weights in the range of 254–368 and an average of 353, various concentrations may be used to achieve the desirable osmoiality and ultrafiltration. Preferably, from 1 to 60 grams per liter of peritoneal dialysis fluid can be used. Added to a standard peritoneal dialysis solution containing physiological salt concentrations, this represents an osmolality range between 280 milliOsmol/kg and 460 milliOsmol/Kg.

In the formulation of dialysis solutions based on hydrogenated trisaccharide which comprise a homogeneous or equimolar mixtures of $[GP]_2$Sorbitol, $[GP]_2$Xylitol, $[GP]_2$Ribitol, and $[GP]_2$Glycerol with the molecular weight in the range of 416–524 and a average of 497, again various concentrations may be used to achieve the desirable osmolality and ultrafiltration. Preferably, from 1 to 60 grams per liter of peritoneal dialysis fluid can be used. Added to a standard peritoneal dialysis solution containing physiological salt concentrations, this represents an osmolality range between 280 milliOsmol/kg and 405 milliOsmol/Kg.

In the formulation of dialysis solution based on hydrogenated di- and trisaccharide equimolar mixture with a molecular weight range of 254–524 and an average of 425, again various concentrations may be used to achieve the desirable osmolality and ultrafiltration. Preferably, from 1 to 60 grams per liter of peritoneal dialysis fluid can be used. Added to a standard peritoneal dialysis solution containing physiological salt concentrations, this represents an osmolality range between 280 milliOsmol/kg and 420 milliosmol/Kg.

Typically, when compared to a 4.25% glucose peritoneal dialysis solution, a formulation based on 4% hydrogenated disaccharides produced a similar ultrafiltration profile at 6 to 7 hours dwell times, and a higher ultrafiltration profile at between 8 and 12 hours dwell times, despite a lower initial osmolality (395 versus 485 milliOsm/Kg). A formulation based on hydrogenated trisaccharide produced a similar ultrafiltration profile at 7–8 hours dwell, and a higher ultrafiltration profile over 10 hours dwell time. Preferably, a hydrogenated disaccharide formulation may be used for peritoneal dialysis with short dwell time during the day, and a trisaccharide formulation may be used for long dwell time for overnight therapy.

The use of hydrogenated oligosaccharide reduces the body load of glucose by approximately 40–60%, resulting in a lower energy uptake. For example, during peritnneal dialysis; with both hydrogenated disaccharide and/or trisaccharide formulations, the circulating free fatty acids (a parameter reflecting the caloric intake) decreased to 50% as compared to use of a glucose peritoneal solution. This may reduce the elevated triglycerides in patients receiving glucose peritoneal dialysis. In addition, the reduction of the circulating high glucose levels in uremic patients may also reduce the risk of the generation of advanced glycated end products, an advantage involving a possible health benefit in the pathology of uremia and in particular in diabetic nephropathy.

Reducing sugars such as glucose, oligosaccharide and polyglucose containing carbonyl groups in the sugar unit react with free amino groups of proteins to form labile Schiff bases that undergo Amadori rearrangement to stable ketoamines. This process is called, glycation and has been found to be increased in diabetes and uremia. The Amadori products undergo very slowly a series of rearrangement reactions (Maillard reactions) resulting in the formation of brown fluorescent and cross-linking glycated proteins or advanced glycation end products (AGE), and play an important role in the process of ageing, diabetic and uremic late complications. In this invention hydrogenated oligosaccharides having the alpha-D-glucosyl arrangement with (1→6) or a (1→4) glucosyl linkages in which the non-reducing sugar at the end of the glucosyl arrangement has been hydrogenated, do not contain a terminal carbonyl group (c.f. oligosaccharides or sugar monohydrates). Because of the lack of terminal carbonyl groups, the Maillard reaction inducing the formation of advanced glycated proteins in the peritoneal cavity does not occur, This has the advantage that the peritoneum matrix and the peritoneal mesothelial and endothelial cells forming the peritoneum membrane are not altered by the possible action of glycated protein, leading to fibrosis and protein cross-linking which may destroy the natural membrane.

Formulations of peritoneal solutions, free of carbohydrates without terminal carbonyl groups may be steam sterilized in physiological pH ranges without the risk of caramelization and the forming of a dark color during industrial processing. Glucose monohydrate and normal oligosaccharides should be maintained during steam sterilization procedures in acid pH ranges of 5.2 to 5.6, to avoid caramelisation of the sugars and reduce the production of sugar degradation products. The use of acidic glucose based peritoneal solution has a cytotoxic effects on the peritoneal cells leading to the alteration and inhibition of the natural immune protection such as bacteria killing properties and cytokine production.

Hydrogenated oligosaccharides have a higher molecular weight than glucose monohydrate, diffuse less rapidly through the peritoneal membrane. For example, the transperitoneal absorption of hydrogenated disaccharides or trisaccharide solution with 1% up to 4% concentrations is reduced by between 20% to 40% compared to a 4.25% glucose solution for a dwell time of 8 hours. The reasons for the low peritoneal absorption of hydrogenated oligosaccharide is probably not solely due to their higher molecular weight but also due to the lack of receptors for hydrogenated oligosaccharide in mesothelial and endothelial cells which would otherwise accelerate transport.

The replacement (or partial replacement) of glucose by oligosaccharide alcohol in a peritoneal dialysis can reduce the requirement for insulin and the body load in glucose is significantly reduced, For instance, after venous infusion of 0.6 grams of a formulation of mixed hydrogenated disaccharides or hydrogenated trisaccharide in rats, the insulin increase is in the average of 50% reduced when compared to the same amount of glucose infusion.

The transperitoneally absorbed hydrogenated oligosaccharides are rapidly metabolized predominantly in the liver by the action acid maltase cell lysosome which acts during the first hour, cleaving 50% of glucose and 50% of polyols for the hydrogenated oligosaccharide formulations, or cleaving 75% of glucose and 25% of polyols for the hydrogenated trisaccharide formulations. Although a large portion of the metabolites are glucose, it does not require insulin for further metabolism. For example, the metabolic response to a venous infusion of 0.6 grams of a formulation of mixed hydrogenated disaccharides or hydrogenated trisaccharide in rat experiments, demonstrated a total metabolism of the hydrogenated oligosaccharide and the resulting end metabolites such as glucose and polyols after 120 minutes. The urinary excretion of all metabolites represented only a maximal portion of 10%, demonstrating that under uremic condition there no risk in the accumulation of hydrogenated disaccharides and hydrogenated trisaccharide. It follows from these this animal experiments that the rate of the transperitoneal adsorption of hydrogenated alpha-D-oligosaccharide with 100% hydrolysis occurring in the first two hours and inducing the cleavage of glucose and polyols can not exceed the polyol metabolic capacity of the body even under uremic conditions.

In the case of the formulation of hydrogenated disaccharide and trisaccharide peritoneal solution at a concentration between 0.1 and 6% providing an osmolality to perform the required ultrafiltration and exchange, the net weight of glucose which is received into the blood circulation after total metabolism is 50% to 76% reduced, compared to a corresponding glucose solution.

Furthermore, in the case of formulation of hydrogenated disaccharide and trisaccharide peritoneal solution at a concentration between 0.1 and 6% providing an osmolality to perform the required ultrafiltration and exchange, the net weight of polyols which are received into the blood circulation after metabolism is 25% to 50%, compared to a corresponding polyol solution such as a glycerol, sorbitol or xylitol solution. Thus, a mixed formulation containing 2 to 3 types of hydrogenated oligosaccharide, as proposed in the preferred aspects of this invention will significantly reduce the net weight of polyols which are received into the blood.

In the case of a homogeneous formulation containing hydrogenated disaccharides at a concentration between 0.1 and 6%, the maximal doses of end metabolites xylitol or sorbitol, or glycerol or ribitol are calculated to be between 10 g/day and 60 g/day. Respectively, a homogeneous formulation containing hydrogenated trisaccharide, will induce a maximal doses between 5g/day and 30 g/day.

In the case of an equimolar mixture containing different hydrogenated disaccharides at a concentration between 0.1 and 6%, the maximal doses of end metabolites xylitol and sorbitol, and glycerol and ribitol are calculated to be between 2.5 g/day and 15 g/day. Similarly, an equimolar mixture containing hydrogenated trisaccharide, will induce a maximal doses between 1.25 g/day and 7.5 g/day. The use of a mixed formulation is preferred, while reducing the risk of the secondary effects associated with polyols.

The use of the hydrogenated oligosaccharides as osmotic agents has advantages in respect to their biocompatibility and cytotoxicity, Since the hydrogenated oligisaccharides can be provided at a more physiological pH, and the hydrogenated oligisaccharides are not metabolized in the peritoneum (forming glucose), no alteration of cell function (such as cell inhibition) tends to take place during therapy, The advantage of the use of hydrogenated disaccharides or hydrogenated trisaccharide, is that these substances are not glycated and do not inhibit the action of alpha-glucosidase. This has the advantages, that long term peritoneal dialysis with hydrogenated oligisaccharides as described in this invention does not induce so-called storage disease. For instance in an in vitro experiment, it can be demonstrated that the incubation of polyglucose (a situation which occurs in the body) inhibits the action of the alpha-glucosidase after six weeks. In contrasts the incubation of hydrogenated oligosaccharide with glucose does not inhibit the action of alpha-glucosidase. The importance of alpha-glucosidase is to cleave the (1→6) and the (1→4) glucosyl linkage, its inhibition may lead to storage diseases involved in the rediculo-endothelial system blockade described by the use of high molecular weight osmotic agents.

The specific use of hydrogenated disaccharides and/or hydrogenated trisaccharides as described in this invention, has the advantage that the metabolites glucose and maltose can be metabolized before the Amadori or the Maillard (non enzymatic reaction) can take place to modify these substances in the blood circulation. The use of hydrogenated oligosaccharide with a higher degree of polymerization (e.g. up to four) are not preferred, because their metabolism is slow and thus glycation can take place in the circulation. The consequences are that inhibition of the alpha glucosidase may occur and reduces the cascade metabolism of the oligosaccharide.

Amino acid materials, preferably a mixture of essential amino acids with a concentration varying between 5 and 35 grams per liter, may be substituted for a portion of the hydrogenated oligosaccharide, to increase the osmolality or to provide a desired amount of nutrition to the patients and to counterbalance the lost of amino acids and peptides in the peritoneum during the therapy. Sulfhydryl-type antioxidants, may be added to stabilize the amino acids. By addition of amino acids, the concentration of hydrogenated oligosaccharide may be reduced to maintain the desired osmotic properties of the peritoneal solution.

The hydrogenated oligosaccharide of the invention may, as indicated, be supplied and used as a dialysis fluid, However, a peritoneal dialysis solution containing hydrogenated oligosaccharides may be prepared in a solid form by freeze drying. Before use in peritoneal dialysis the dry material is reconstituted by dissolution in sterile and pyrogen free water.

Thus in accordance with a further aspect of the invention there are provided compositions for use in preparing a peritoneal dialysis fluid as defined herein, by reconstitution by addition of sterile, pyrogen free water, said composition comprising the specified components in dry form or in the form of an aqueous concentrate.

The invention further provides a method of performing peritoneal dialysis which comprises perfusing the peritoneal membrane with a peritoneal dialysis fluid as defined herein.

Additionally, the invention provides the use of a compound of Formula

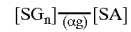

in the manufacture of a peritoneal dialysis fluid.

BRIEF DESCRIPTION OF THE DRAWINGS

Additionally reference will be made to the accompanying drawings of which

FIGS. 2 to 9 illustrate graphically and diagramatically the results of experiments described in experimental procedures 1–4.

Figure 1:
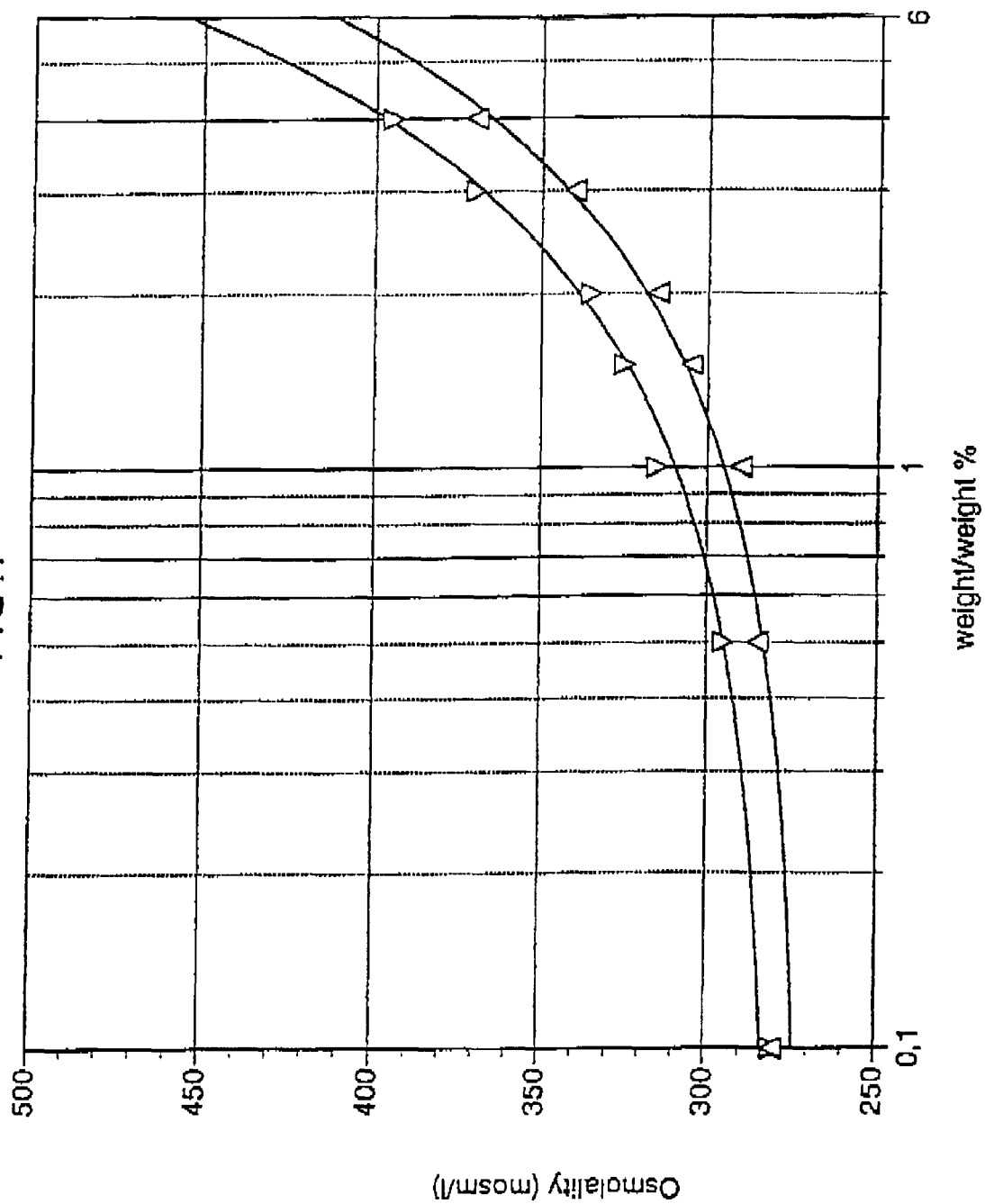
FIG. 1 illustrates the relationship between osmolality and concentration for specified hydrogenated di- and tri-saccharide mixtures.

The invention will now be described, by was of illustration without limitations, in the following examples and in vivo and in vitro experimental procedures.

EXAMPLE 1

A solution for peritoneal dialysis having an osmolality of about 395 milliosmols per liter of water can be prepared by mixing 5.786 grams of sodium chloride, 3.925 grams per liter of sodium lactate, 0.2573 grams per liter of calcium chloride, 0.1017 grams per liter of magnesium chloride, and 40 grams of a [GP]sorbitol (hydrogenated disaccharide). The solution will be sterilized in conventional manner as prescribed for parenteral solutilis.

EXAMPLE 2

A solution for peritoneal dialysis having an osmolality of about 395 milliosmols per liter of water can be prepared by mixing 5.786 grams of sodium chloride, 2.940 grams per liter of sodium bicarbonate, 0.2573 grams per liter of calcium chloride, 0.1017 grams per liter of magnesium chloride, and 40 grams of a [GP]sorbitol (hydrogenated disaccharide). The solution will be sterilized in conventional manner as prescribed for parenteral solutions.

EXAMPLE 3

A solution for peritoneal dialysis having an osmolality of about 395 milliosmols per liter of water can be prepared by mixing 5.786 grams of sodium chloride, 3.850 grams per liter of sodium pyruvate, 0.2573 grams per liter of calcium chloride, 0.1017 grams per liter of magnesium chloride, and 40 grams of a [GP]sorbitol (hydrogenated disaccharide). The solution will be sterilized in conventional manner as prescribed for parenteral solutions.

EXAMPLE 4

A solution for peritoneal dialysis having an osmolality of about 395 milliosmols per liter of water can be prepared by mixing 5.493 grams of sodium chloride, 1.100 grams per liter of sodium pyruvate and 2.520 of sodium bicarbonate, 0.2573 grams per liter of calcium chloride, 0.1017 grams per liter of magnesium chloride, and 40 grams of a [GP]sorbitol (hydrogenated disaccharide). The solution will be sterilized in conventional manner as prescribed for parenteral solutions.

EXAMPLE 5

A solution for peritoneal dialysis having an osmolality of about 400 milliosmols per liter of water can be prepared by mixing 5.786 grams of sodium chloride, 3.925 grams per liter of sodium lactate, 0.2573 grams per liter of calcium chloride, 0.1017 grams per liter of magnesium chloride, and 40 grams of an equimolar mixture of [GP]sorbitol, [GP]xylitol, and [GP]glycerol, The solution will be sterilized in conventional manner as prescribed for parenteral solutions.

EXAMPLE 6

A solution for peritoneal dialysis having an osmolality of about 400 milliosmols per liter of water can be prepared by mixing 5.786 grams of sodium chloride, 2.940 grams per liter of sodium bicarbonate, 0.2573 grams per liter of calcium chloride, 0.1017 grams per liter of magnesium chloride, and 40 grams of an equimolar mixture of [GP]sorbitol, [GP]xylitol, and [GP]glycerol. The solution will be sterilized in conventional manner as prescribed for parenteral solutions.

EXAMPLE 7

A solution for peritoneal dialysis having an osmolality of about 400 milliosmols per liter of water can be prepared by mixing 5.786 grams of sodium chloride, 3.850 grams per liter of sodium pyruvate, 0.2573 grams per liter of calcium chloride, 0. 1017 grams per liter of magnesium chloride, and 40 grams of an equimolar mixture of [GP]sorbitol, [GP]xylitol, and [GP]glycerol. The solution will be sterilized in conventional manner as prescribed for parenteral solutions.

EXAMPLE 8

A solution for peritoneal dialysis having an osmolality of about 400 milliosmols per liter of water can be prepared by mixing 5.493 grams of sodium chloride, 1.100 grams per liter of sodium pyruvate and 2.520 of sodium bicarbonate, 0.2573 grams per liter of calcium chloride, 0.1017 grams per liter of magnesium chloride, and 40 grams of an equimolar mixture of [GP]sorbitol, [GP]xylitol, and [GP]glycerol. The solution will be sterilized in conventional manner as prescribed for parenteral solutions.

EXAMPLE 9

A solution for peritoneal dialysis having an osmolality of about 370 milliosmols per liter of water can be prepared by mixing 5.786 grams of sodium chloride, 3.925 grams per liter of sodium lactate, 0.2573 grams per liter of calcium chloride, 0.1017 grams per liter of magnesium chloride, and 40 grams of a $[GP]_2$sorbitol (hydrogenated trisaccharide). The solution will be sterilized in conventional manner as prescribed for parenteral solutions.

EXAMPLE 10

A solution for peritoneal dialysis having an osmolality of about 370 milliosmols per liter of water can be prepared by mixing 5.786 grams of sodium chloride, 2.940 grams per liter of sodium bicarbonate, 0.2573 grams per liter of calcium chloride, 0.1017 grams per liter of magnesium chloride, and 40 grams of a $[GP]_2$sorbitol (hydrogenated trisaccharide). The solution will be sterilized in conventional manner as prescribed for parenteral solutions.

EXAMPLE 11

A solution for peritoneal dialysis having an osmolality of about 370 milliosmols per liter of water can be prepared by mixing 5.786 grams of sodium chloride, 3.850 grams per liter of sodium pyruvate, 0.2573 grams per liter of calcium chloride, 0.1017 grams per liter of magnesium chloride, and 40 grams of a $[GP]_2$sorbitol (hydrogenated trisaccharide). The solution will be sterilized in conventional manner as prescribed for parenteral solutions.

EXAMPLE 12

A solution for peritoneal dialysis having an osmolality of about 370 milliosmols per liter of water can be prepared by mixing, 5.493 grams of sodium chloride, 1.100 grams per liter of sodium pyruvate and 2.520 of sodium bicarbonate, 0.2573 grams per liter of calcium chloride, 0.1017 grams per liter of magnesium chloride, and 40 grams of a [GP]$_2$sorbitol (hydrogenated trisaccharide). The solution will be sterilized in conventional manner as prescribed for parenteral solutions.

EXAMPLE 13

A solution for peritoneal dialysis having an osmoticality of about 375 milliosmols per liter of water can be prepared by mixing 5.786 grams of sodium chloride, 3.925 grams per liter of sodium lactate, 0.2573 grams per liter of calcium chloride, 0.1017 grams per liter of magnesium chloride, and 40 grams of an equimolar mixture of [GP]$_2$sorbitol, [GP]$_2$xylitol, and [GP]$_2$glycerol. The solution will be sterilized in conventional manner as prescribed for parenteral solutions.

EXAMPLE 14

A solution for peritoneal dialysis having an osmolality of about 375 milliosmols per liter of water can be prepared by mixing 5.786 grams of sodium chloride, 2.940 grams per liter of sodium bicarbonate, 0.2573 grams per liter of calcium chloride, 0.1017 grams per liter of magnesium chloride, and 40 grams of an equimolar mixture of [GP]$_2$sorbitol, [GP]$_2$xylitol, and [GP]$_2$glycerol. The solution will be sterilized in conventional manner as prescribed for parenteral solutions.

EXAMPLE 15

A solution for peritoneal dialysis having an osmolality of about 375 milliosmols per liter of water can be prepared by mixing 5.786 grams of sodium chloride, 3.850 grams per liter of sodium pyruvate, 0.2573 grams per liter of calcium chloride, 0.1017 grams per liter of magnesium chloride, and 40 grams of an equimolar mixture of [GP]$_2$sorbitol, [GP]$_2$xylitol, and [G3P]$_2$glycerol. The solution will be sterilized in conventional manner as prescribed for parenteral solutions.

EXAMPLE 16

A solution for peritoneal dialysis having an osmolality of about 375 milliosmols per liter of water can be prepared by mixing 5.493 grams of sodium chloride, 1.100 grams per liter of sodium pyruvate and 2.520 of sodium bicarbonate, 0.2573 grams per liter of calcium chloride, 0.1017 grams per liter of magnesium chloride, and 40 grams of an equimolar mixture of [GP]$_2$sorbitol, [GP]$_2$xylitol, and [GP]$_2$glycerol. The solution will be sterilized in conventional manner as prescribed for parenteral solutions.

Experimental Procedure 1

The purpose of this experiment was to evaluate the proposed dialysis solutions with hydrogenated oligosaccharide in a rat model.

Male Normal rats weighing 250–400 g were used in all the experiments. Briefly, the animals were anaesthetized with pentobarbital sodium (35 mg/Kg intraperitoneal), placed on a heating pad (37° C.) and maintained under anaesthesia with 20 mglkg injections in the neck region. A 16-gauge catheter was introduced in the peritoneal cavity, and a volume of 15 ml dialysate at 37° C. temperature was injected. After 1, 2, 3, 4, 5, 6, 8, 10 and 12 hours, the animals were weighed and blood samples were taken for analysis. For each time points 3 animals were investigated. The fluid in the peritoneum was taken using a syringe by opening the abdomen, after the animals were sacrificed and exsanguinated.

The dialysate solutions were: A a hypo-osmolar control lactated Ringer's solution with an osmolality of 255 mOsm/Kg; B: a hyper-osmolar standard 4.25% glucose peritoneal dialysis solution (Fresenius Medical care) with an osmolality of 504 mOsm/Kg; C: a 4% hydrogenated disaccharides peritoneal dialysate as formulated in Example 5; D: a 4% hydrogenated trisaccharide peritoneal dialysate as formulated in Example 13. The substances [GP]sorbitol, [GP]xylitol, [GP]glycerol, [GP]$_2$sorbitol, [GP]$_2$xylitol and [GP]$_2$glycerol were prepared as described[17-21]. The Osmolality of the 4% solution C was 395 mOsm/Kg and respectively of the osmolality of solution D was 370 mOsm/Kg as measured by the freezing point method. For instance, FIG. 1 shows the osmolality function of both C and D formulations by varying the concentration of the hydrogenated oligosaccharide.

Figure 2:
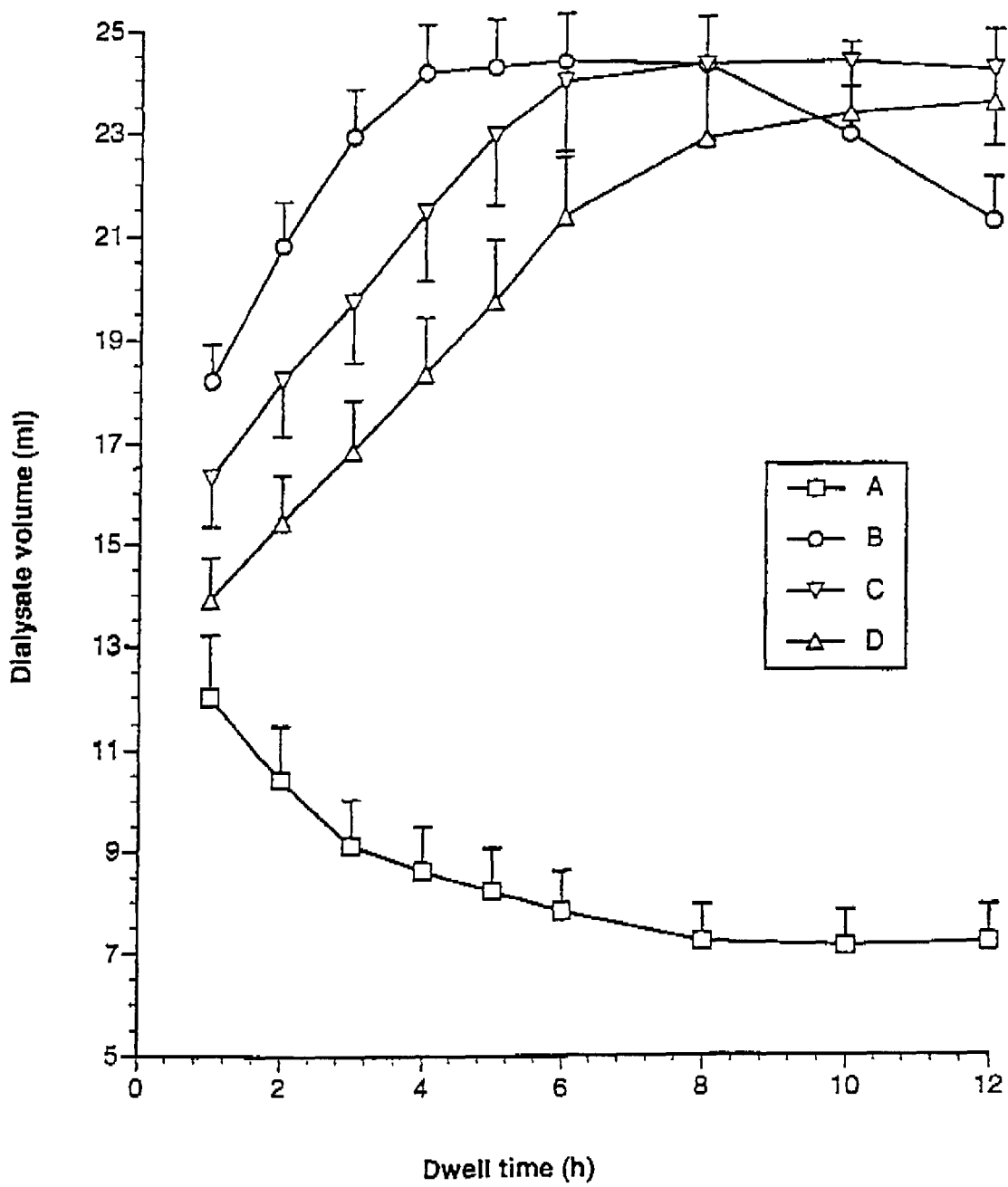

FIG. 2 shows the peritoneal dialysate volumes as a function of the dwell time. It was demonstrated, that solutions D, C and D induced a transperitoneal ultrafiltration demonstrated by an increase in the peritoneal volume profiles, No ultrafiltration occurred with the hypo-osmolar control solution A. When compared to the 4.25% glucose solution B), the solution C produced similar ultrafiltration profile after 6 hours dwell time, despite a lower initial ultrafiltration during the first 4 hours of dwell time. On the other hand, the solution D produced similar ultrafiltration as solution B, after 10 hours dwell times did not decreased over the period of 12 hours dwell times. Both solutions C and D, have the advantages that their ultrafiltration profiles. In contrast, the ultrafiltration profile of 4.25% glucose solution decreased after 6 to 8 hours dwell time suggesting the starting of a negative ultrafiltration rate.

Figure 3:
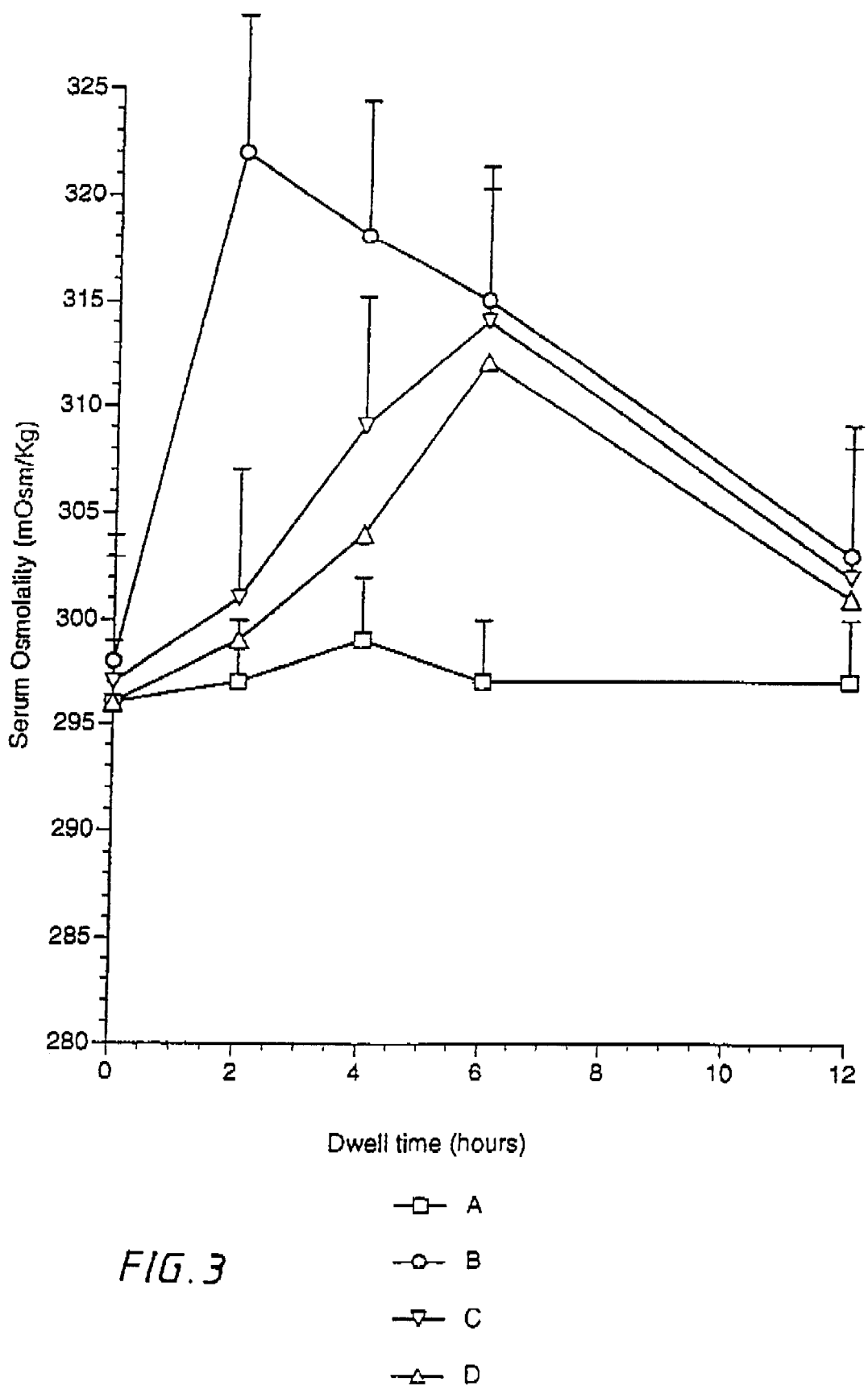

Results from FIG. 3 shows the serum osmolalities during the study time, which a marker for the uptake and time related metabolisms of the osmotic agents. The increase in serum osmolality for the 4.25% glucose solution occurred after 2 hours dwell time. For the solutions C and D, the serum osmolality increased after 6 hours. For both solutions C and D, maximal increase in serum osmolality relative to the values before intraperitoneal injection were between 5 and 6%. However these increases in the serum osmolality was less that those (9.4%) observed induced by the 4.25% glucose dialysis (Solution B).

Figure 4:
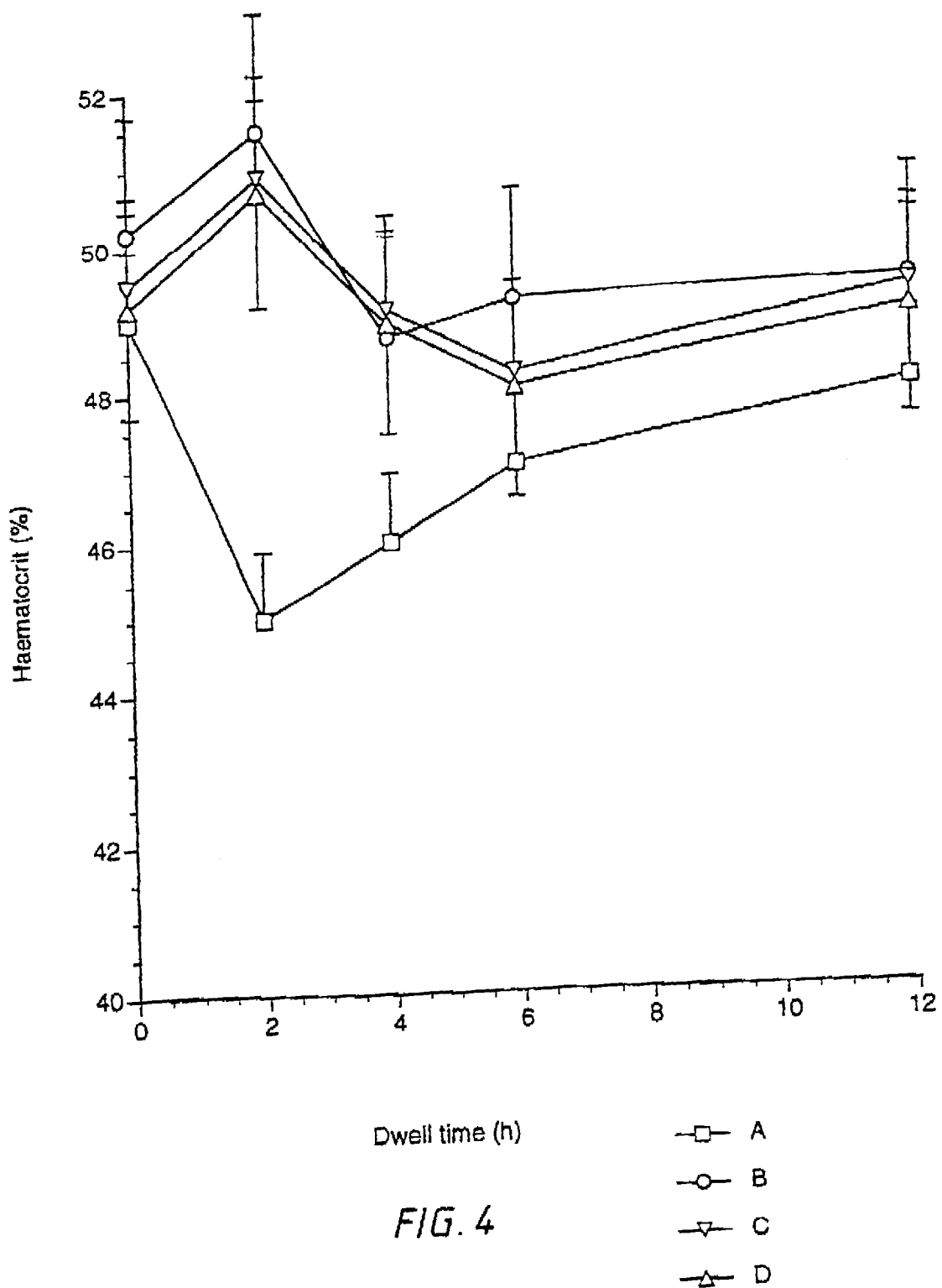

Results from FIG. 4 shows the blood hematocrit, demonstrating only minor changes for all solutions.

Conclusion: Both hydrogenated disaccharides and trisaccharide showed an ultrafiltration profile which is quantitatively comparable to that obtained by an hyper-osmolar 4.25% glucose dialysate. However, the ultrafiltration rates during the entire dwell time of 8 to 12 hours for both hydrogenated disaccharides and trisaccharide were superior to those obtained by the glucose solution.

Experimental Procedure 2

The purpose of the study described the metabolic responded to intravenous administration of hydrogenated disaccharides (Example 5) and hydrogenated trisaccharide (Example 13). The hydrogenated oligosaccharide were prepared as described[17-21]. The experiments were designed to analyze the metabolic response over the period of 120 min. The injection doses were the total amount contained in 15 ml of dialysate, which represents the average of 1.85 g/kg of body weight, Male Wistar rats weighing 250–400 g were used in all the experiments. The animal were anaesthetized with pentobarbital sodium (35 mg/Kg intraperitoneal). An intravenous dose of 0.6 gr in 3 ml volume of investigated substances were administrated on the femoral vein inguinal during the period of 10 minutes. The femoral artery was cannulated for blood sampling taken at a period of 15 min of time. Measurements of [GP]sorbitol, [GP]xylitol, [GP]glycerol, [GP]$_2$sorbitol, [GP]$_2$xylitol, and [GP]$_2$glycerol, sorbitol, xylitol and glycerol were performed by gaschromatography using the acetyl derivation. Blood plasma samples were assayed for free fatty acids (FFA), glucose by glucose oxidase method, insulin by charcoal immunoassay analysis. Urine was collected for 2 hour after venous infusion.

Results from FIGS. 5 and 6 show the metabolic responses to intravenous loading of 0.6 gr of glucose (B), of an equimolare mixture of [GP]sorbitol, [GP]xylitol, and [GP]glycerol (C), [GP]$_2$sorbitol, [GP]$_2$xylitol, and [Gp]$_2$glycerol (D). The control solution was 0.6 g of the salts from the lactated Ringer. Results demonstrated that after injection of both C and D, there was no significant increase in serum glucose during the entire 120 min interval, the blood glucose concentrations increased to 30% over the initial values. In contrast. After glucose injections, blood glucose increased to 160%. As demonstrated, both hydrogenated disaccharides and trisaccharide, were well utilized probably due to alpha-glucosidase activity. During the entire interval of 120 min time, the total doses of 1.85 g/kG hydrogenated oligosaccharide were metabolized. The serum insulin concentration increased to 2.8 to 3.1-fold rise. Subsequent concentrations of serum insulin were similar for both hydrogenated oligasaccharide. Following the infusion of substances C and D). Following glucose infusion, there was a 5-fold increase in serum insulin. A drop in plasma FFA was noted after infusion of B, C, and D. However, the drop initiated by glucose was significantly ($p<0.01$) stronger than the drops induced by both hydrogenated oligosaccharide, suggesting that the caloric intake was less than for glucose.

FIG. 7 shows the metabolic response in the serum polyol levels and the urinary excretion of all metabolites of [GP]sorbitol, [GP]xylitol, and [GP]glycerol, [GP]$_2$sorbitol, [GP]$_2$xylitol, and [GP]$_2$glycerol, Results demonstrated that all polyols were totally metabolized during the entire time of 120 min. The urinary excretion of all possible metabolites of the hydrogenated disaccharides and trisaccharide were under 9% of the injected doses, suggesting that the metabolism occurred mainly in the body.

Conclusion: The ability of the rats to metabolize circulating hydrogenated disaccharides and trisaccharide suggests that these substances can be used as osmotic agents in peritoneal dialysis. In addition the results demonstrated that these substances need less insulin.

Experimental Procedure 3

The purpose of the study described the cytotoxic effects of hydrogenated oligosaccharide in a model of monocytes. This an in vitro model enable to evaluate the inhibition of the cell function following exposition with possible toxic substances.

Experiments have been performed according to the protocol previously published[22]. Briefly, Peripheral blood mononuclear cells (PBMC) from healthy human donors were separated by density centrifugation (Ficoll-Hypaque. The phase containing PBMC was collected, washed with saline, counted, and resuspended in RPMI (Rooswelt Park Memorial Medium) at the desired concentration. The cytotoxic effects following exposition of PBMC with the dialysate were analyzed as follow: 1) For the Superoxyd anion ($O_2$.) determination, PBMC were incubated for 15 mins with the test solutions, thus the cells were washed and incubated with opsonized zymosan. Superoxyd dismutase inhibitable $O^2$-radical formation was determined by the reduction of Cytochrome C at 546 nm; 2) for the cytokine tests, cells were exposed to the sterile solutions for 15 mins and resuspended in sterile RPMI, stimulated with endotoxin (1 ng/ml), and incubated at 37° C. in a 5% $CO_2$ Atmosphere for 24 hours. Cell were lysed and assayed for Interleukin-1β.

The test solutions were the hydrogenated disaccharide solution from Example 6 and from Example 8. Control solution were the 4.25% glucose solutions.

Results from FIG. 8 demonstrated that both glucose free solutions (Example 6 and 8) have no effects on the PBMC function as determined by the oxygen free radicals and cytokine production. In contrast the glucose solutions inhibited the PBMC by a 80–90% reduction on the cell activities.

Conclusion: glucose free hydrogenated oligosaccharide solutions have no effects on the cell functions and represent an advantage in respect to the biocompatibility of peritoneal dialysis solutions.

Experimental Procedure 4

The purpose of the study described the influence of Amadori and Maillard products on the alpha-glucosidase. The in vitro model evaluated the generation of Maillard products by incubation of the 4% hydrogenated disaccharides (Example 9) and 4% hydrogenated trisaccharide. Control experiments were the 4.25% glucose and 7% polyglucose (icodextrin-Baxter) containing solutions.

50 mg/ml of albumin were incubated in vitro during 6 weeks with test dialysate solution to generate advanced glycated end products (AGE). AGE were measured after each week of incubation. Following the incubations, the samples were further incubated for 2 hours at 37° C. with alpha-glucosidase (from Saccharomyces cerevisae) and $C^{14}$ labelled maltose and a pentasaccharides. The alpha-glucosidase activity was evaluated by the cleavage of the labeled oligosaccharide using high performance chromatography (HPLC).

FIG. 9 demonstrated that both glucose and polyglucose containing dialysate solution generated Maillard products. However, polyglucose induced by weight less Maillard products than glucose containing solutions. In contrast, the hydrogenated oligosaccharide for which the carbonyl groups were reduced, no generation of AGE occurred. The alpha-glucosidase are inhibited through the Maillard- (and Amadori) compounds induced by Icodextrin but not through glucose.

REFERENCES

1 Mahiout A, Ehlerding G, Brunkhorst R. Nephral Dial Transplant, 5, 2–6 1996
2 Twardowsky Z J, Moore H L, McGary T J, Poskuta M, Stathkis C, Hirszel P. Perit Dial Bull 4 (3): 125; 1984
3 Raja R S, Kramer M S, Manchanda R, Lazaro N, Rosenbaum J L. Ann Intern Med 79;511; 1973
4 Bazzato G, Coli U, Landini S et al. Perit Dial Bull 2: 161; 1982
5 Yatuc W, Ward G, Shiepetar G, Tenckoff H. Trans Am Soc Artif Intern Organs 13; 168; 1967
6 Higgins J T, Cross M L, Somani P. Prit Dial Bull 4: 131; 1984
7 Winchester J F, Stegink L D, Ahmad S at al. In frontiers in Peritoneal Dialysis, edited by Maher J F, Winchester J F, New York, Field, Rich snd Associates Inc, 1986, p 231
8 Mistry C D, Mallick N P, Gokal R. Lancet ii: 178–182; 1982
9 Gjessing J. Lancet ii 82, 1968
10 De Paepe M, Matthijis E, Peluso F et al. In Prevention and Treatment of Diabetic Nephropathy, edited by Keen H, Legrain M, Boston, MTP Press Ltd, 1983, p 299
11 Klein E, Ward RA, Williams TE, Feldhoff PW, Trans Am Soc Artif Intern Organs 32: 550, 1986
12 Twardowski Z J, Hain H, McGary T J, Moore H L, Keller R S. In Frontiers in Peritoneal Dialysis, edited by Mahler J F, Winchester J F, New York, Field, Rich and Associates Inc, 1986, p 249

13 Schildt B, Bouveng R, Sollenberg M. Acta Chir Scand 141: 7, 1975
14 Johns M Y, Weser W. J. Clin. Invest. 50: 986; 1971
15 Grupp U, Siebert G. Res. Exp. Med 173: 261–278; 1978
16 Wolfrom M. L. Thomson A., O'Neil A. N.,Galkowski T. T.: J. Amer. Chem. Soc, 74, 1062–1064, 1952
17 Garu W., Kurz J., Fischer E., Steinle G., grupp U., Siebert G. Z. Lebensm. Unters. Forsch. 168, 125–130: 1979
18 Ducan, Manners, and Thomson, Biochem J., 73, 296; 1959
19 Sawai and Hehre. J. Biol. Chem, 237: 2047, 1962
20 Lindberg, Acta, Scan, 7: 1119; 1953
21 Fischer and Seyferth, Hoppe-Seyler's. Z. Physiolo. Chem, 349: 1662; 1968
22 Mahiout A, Matata B M, Brunkhorst R. Kidney International 51: 860–867; 1997

Figure Legends

FIG. 1
Osmolality of C: 4% hydrogenated disaccharide mixture an (equimolar mixture of GPSorbitol, GPXylitol, GPGlycerol); D: 4% hydrogenated trisaccharides (equimolar mixture [GP]$_2$Sorbitol, [GP]$_2$Xylitol; [GP]$_2$Glycerol).

FIG. 2
Peritonea dialysate volume as a function of dewll time in animals (rats) injected with 15ml of: A: a lactated Ringer's solution; B: a 4.25% glucose solution; C: 4% hydrogenated disaccharide mixture (equimolar mixture of GPSorbitol, GPXylitol, GPGlycerol); C: 4% hydrogenated trisaccharides (equimolar mixture of [GP]$_2$Sorbitol, [GP]$_2$XylitoI; [GP]$_2$Glycerol). For each group (A, B, C, D) 3×9 rats were injected with 15 ml of peritoneal dialysis solution. For each hour dwell time the dialysate was withdrawn and its volume, measured.

FIG. 3
Serum osmolality (mOsm/Kg) as a function of dwell time in animals (rats) injected with 15 ml of: A: a lactated Ringer's solution; B a 4.25% glucose solution; C: 4% hydrogenated disaccharide mixture (equimolar mixture of GPSorbitol, GPXylitol, GPGlycerol); D: 4% hydrogenated trisaccharides (equimolar mixture of [GP]$_2$Sorbitol, [GP]$_2$Xylitol; [GP]$_2$Glycerol). For each group (A, B, C, D) 3×9 rats were injected with 1 5 ml of peritoneal dialysis solution. For each hour dwell time the dialysate was withdrawn and its volume measured.

FIG. 4
Blood hematocrit as a function of dwell time in animals (rats) injected with 15 ml of: A: a lactated Ringer's solution; B a 4.25% glucose solution; C: 4% hydrogenated disaccharide mixture (equimolar mixture of GPSorbitol, GPXylitol, GPGlycerol); D: 4% hydrogenated trisaccharides (equimolar mixture of [GP]$_2$Sorbitol, [GP]$_2$Xylitol; [GP] Glycerol). For each group (A, B, C, D) nine rats were injected with 15 ml of peritoneal dialysis solution. For each hour dwell time the dialysate was withdrawn and its volume measured.

FIGS. 5(A) and 5(B)
Metabolic response to Intravenous Administration of hydrogenated oligosaccharides in rats: A: 0,6 gr a lactated Ringer; B: 0,6gr gluocose C: 0.6 gr hydrogenated disaccharide mixture (equimolar mixture of GPSorbitol, GPXylitol, GPGlycerol); D: 0,6 g hydrogenated trisaccharides (equimolar mixture of [GP]$_2$Sorbitol, [GP]$_2$Xylitol; [GP]$_2$Glycerol).

FIGS. 6(A) and 6(B)
Metabolic response to Intravenous Administration of hydrogenated oligosaccharides in rats: A: 0,6 gr a lactated Ringer: B: 0,6 gr gluccose C: 0.6 gr hydrogenated disaccharide mixture (equimolar mixture of GPSorbitol, GPXylitol, GPGlycerol); D: 0,6 g hydrogenated trisaccharides (equimolar mixture of [GP]$_2$Sorbitol, [GP]$_2$Xylitol; [GP]$_2$Glycerol)

FIGS. 7(A) and 7(B)
Metabolic response and urinary excretion to Intravenous Administration of hydrogenated oligosaccharides in rats; C: 0.6 gr hydrogenated disaccharide mixture (equimolar mixture of GPSorbitol, GPXylitol, GPGlycerol); D: 0,6 g hydrogenated trisaccharides (equimolar mixture to [GP]$_2$Sorbitol, [GP]$_2$Xylitol; [GP]$_2$Glycerol).

FIG. 8
Mean (±SD) of Zymosan stimulated O2-production in and endotoxin stimulated IL-1β in PBMC after 15 min. exposure to different CAPD solutions.

FIGS. 9(A) and 9(B)
AGE-formation after incubation of 50 mg/ml Albumin with different CAPD-solution and the resulting effect on alpha-glucosidase activity.

Figure 10:
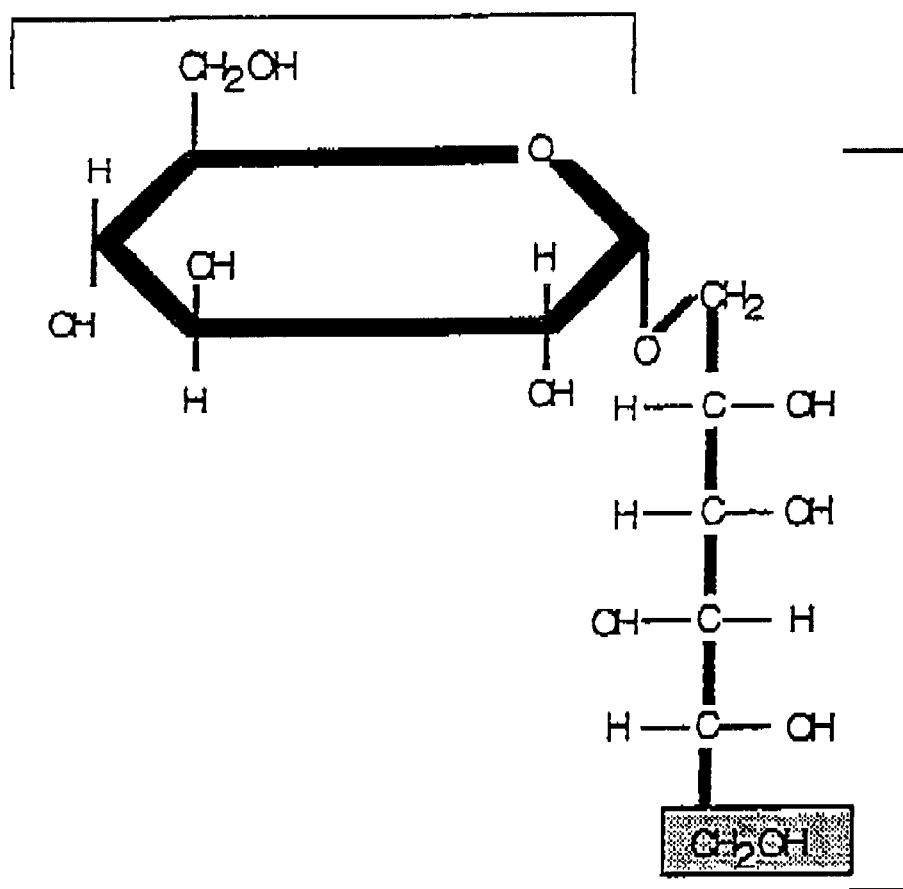
FIGS. 10 to 15 illustrate the structures of representative sugar derivatives suitable for use in accordance with the invention.

FIGS. 10
O, α, D Glucopyranosido-(1→6) Sorbitol.

Figure 11:
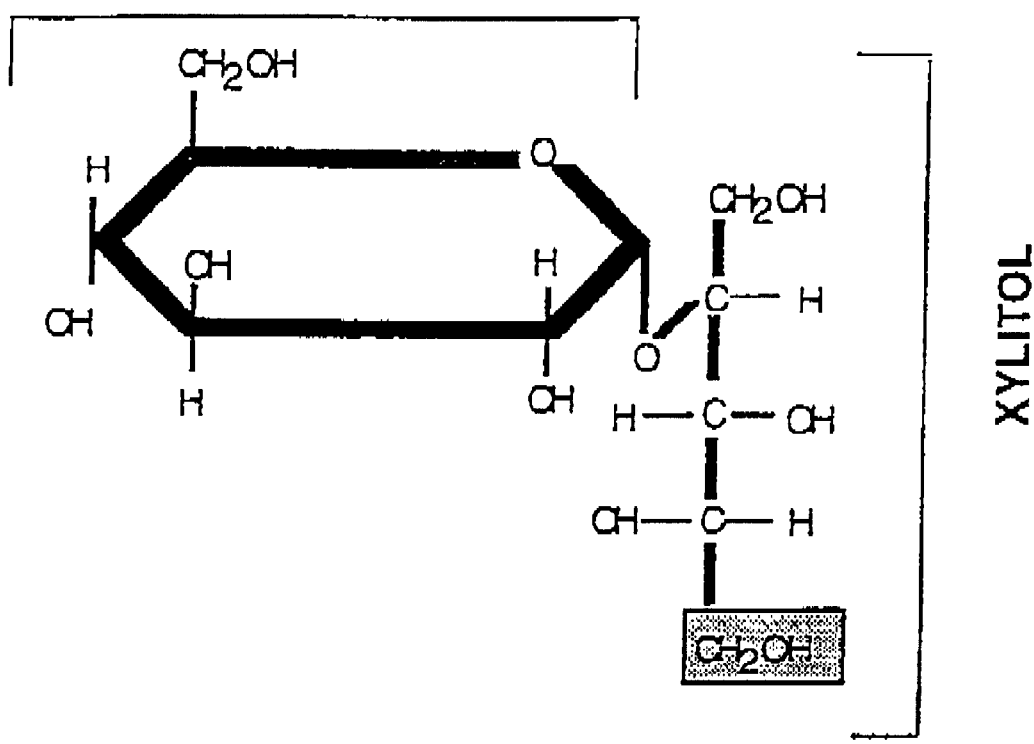

FIGS. 11
O, α, D Glucopyranosido-(1→4) Xylitol.

Figure 12:
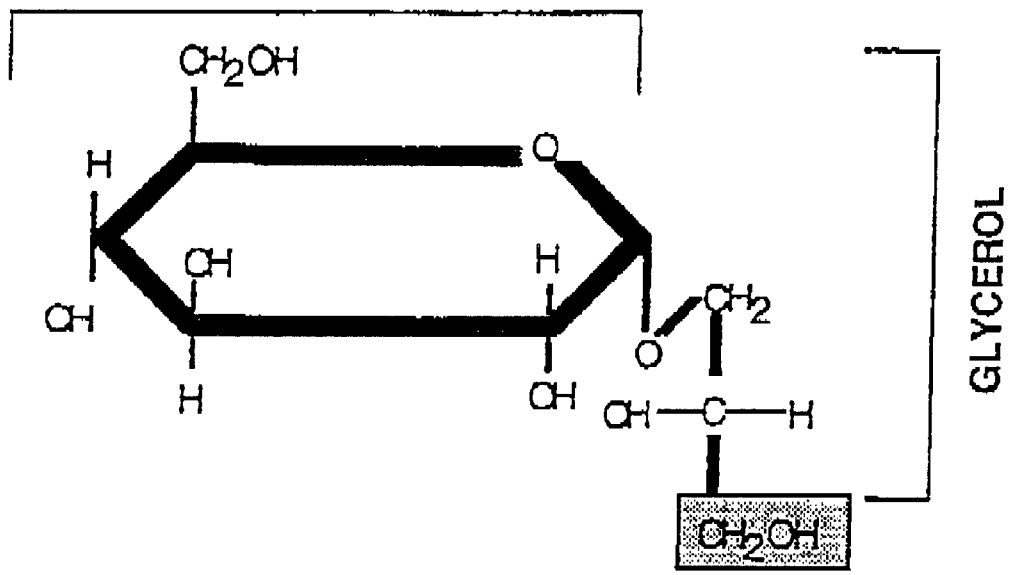

FIG. 12
O, α, D Glucopyranosido-(1→1) Glycerol.

Figure 13:
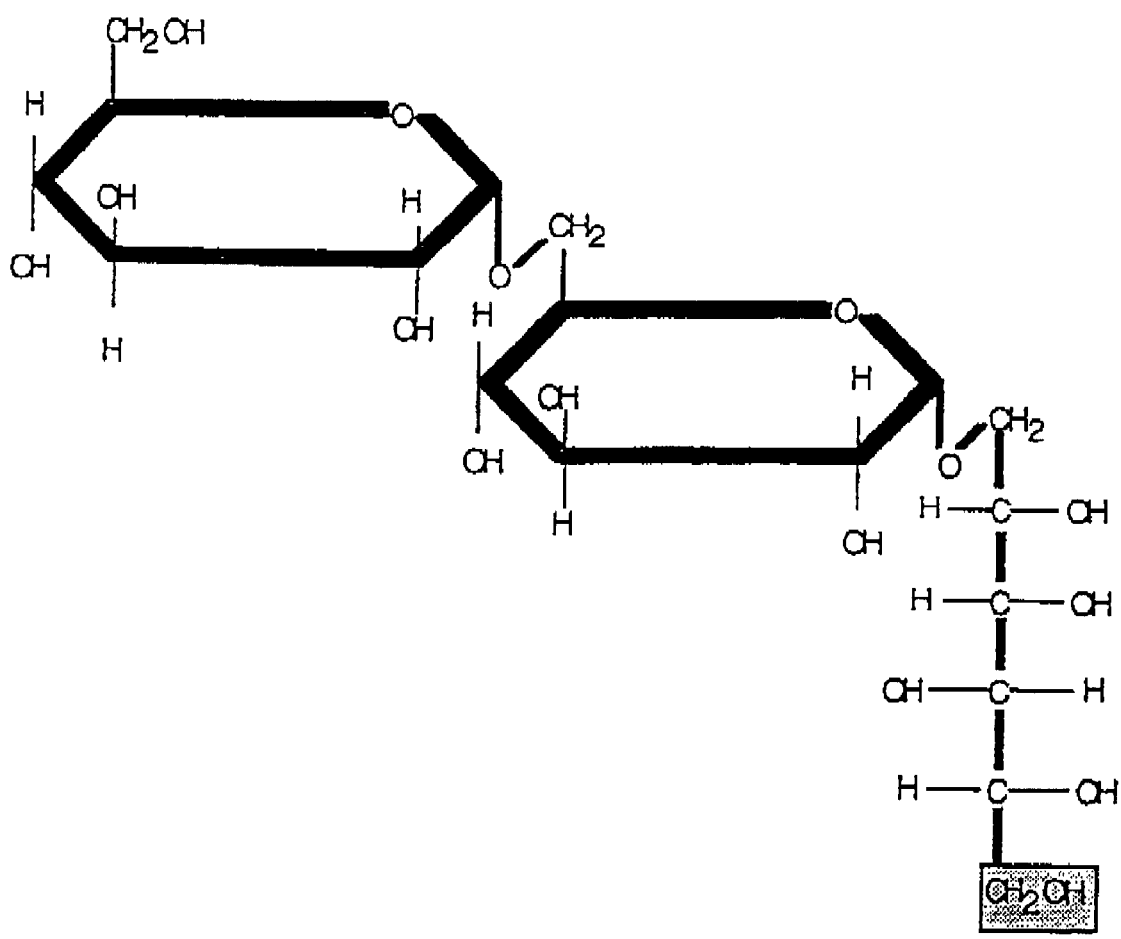

FIG. 13
O, α, D Glucopyranostdo-(1→6) O, α, D Glucopyranosido-(1→6) Sorbitol.

Figure 14:
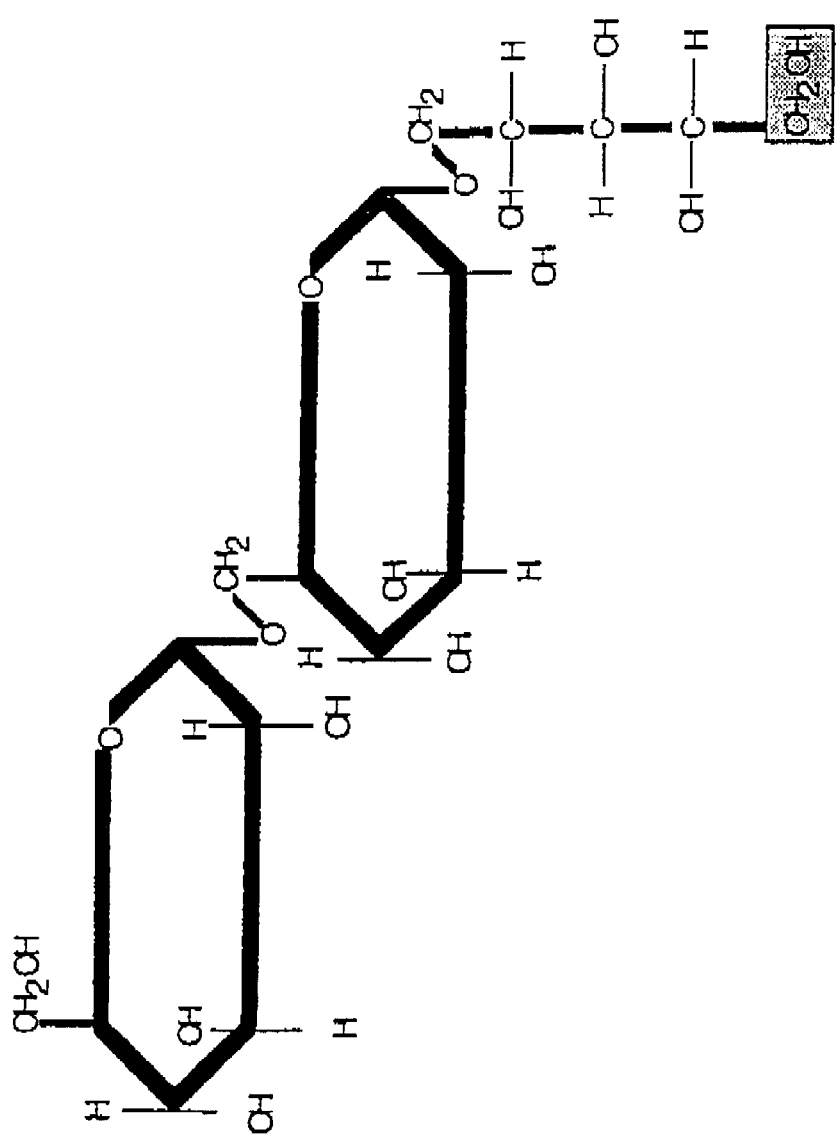

FIG. 14
O, α, D Glucopyranosido-(1→6) O, α, D Glucopyranosido-(1→6) Xylitol.

Figure 15:
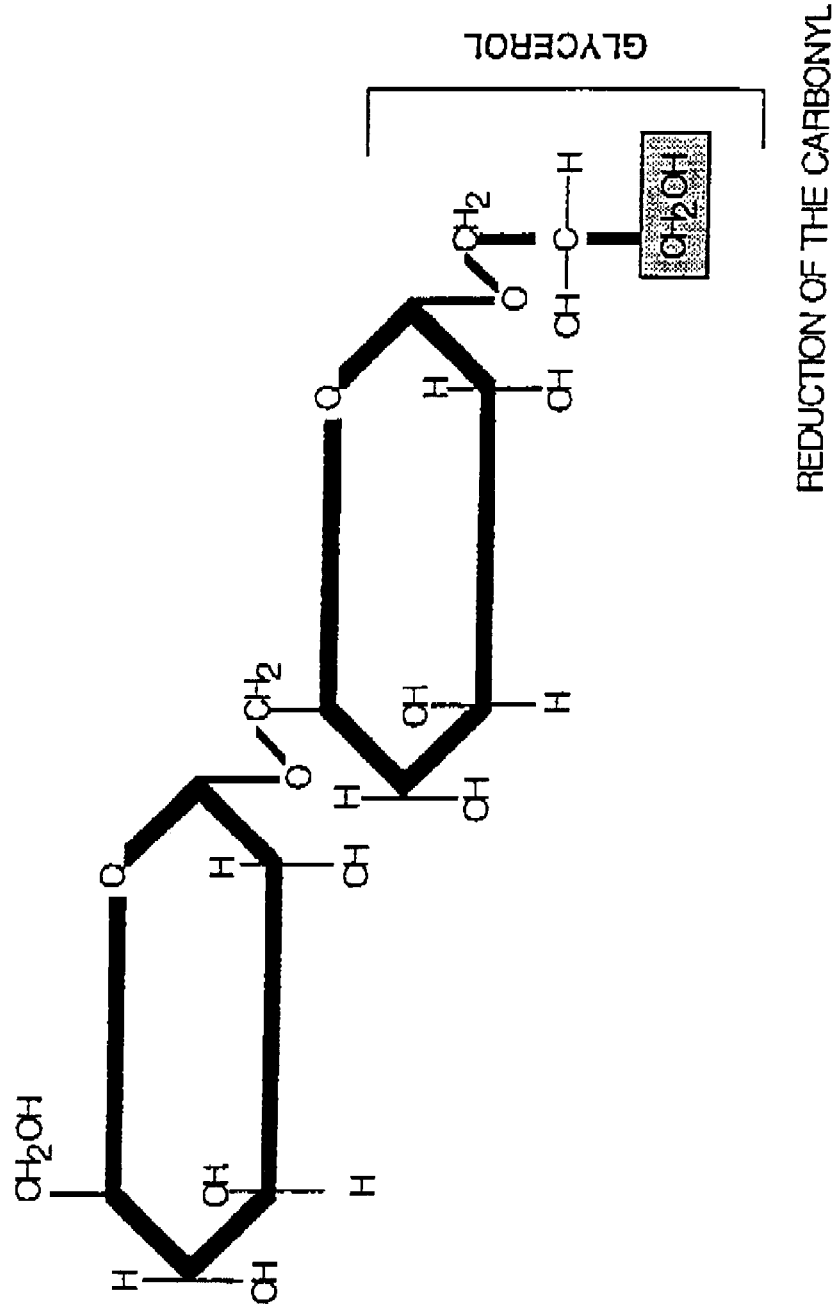

FIG. 15
O α, D Glucopyranosido-(1→6) O, α, D Glucopyranosido-(1→1) Glycerol.

What is claimed is:

1. A peritoneal dialysis fluid comprising a physiologically acceptable aqueous solution comprising physiologically acceptable inorganic anions and cations and at least one sugar derivative as an osmotic agent, said physiologically acceptable inorganic anions and cations and said at least one sugar derivative being present in concentrations sufficient for the removal of water and solutes from a patient by peritoneal dialysis, wherein the sugar derivative is a compound of the formula

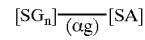

wherein each SG, which may be the same or different, represents a residue of a physiologically acceptable metabolizable sugar, SA represents a residue of a physiologically acceptable metabolizable sugar alcohol, n is 2, and $_{(\alpha g)}$ represents a glycoside linkage that is cleavable by an α-glycosidase enzyme.

2. The peritoneal dialysis fluid according to claim 1, wherein each SG represents a glucose residue.

3. The peritoneal dialysis fluid according to claim 1, wherein the compound of formula

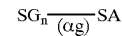

is a hydrogenated trisaccharide.

4. The peritoneal dialysis fluid according to claim 1, wherein SA represents a residue of a sugar alcohol selected from the group consisting of sorbitol, xylitol, ribitol and glycerol.

5. The peritoneal dialysis fluid according to claim 1, having a pH in the range from 5.4 to 7.4.

6. The peritoneal dialysis fluid of claim 5, wherein the pH is in the range of 7.0 to 7.4.

7. The peritoneal dialysis fluid according to claim 1, containing the following concentrations of specified inorganic ions:

| | | |
|---|---|---|
| $Na^+$ | 116–140 | mEq/l |
| $Ca^+$ | 0–5 | mEq/l |
| $Cl^-$ | 100–144 | mEq/l. |

8. The peritoneal dialysis fluid according to claim 1, containing a total of 5 to 40 mEq/l of buffering counterions selected from the group consisting of bicarbonate, pyruvate and lactate ions.

9. The peritoneal dialysis fluid according to claim 1, containing from 1 to 60 g/l of said sugar derivative.

10. The peritoneal dialysis fluid according to claim 9, containing from 10 to 50 g/l of said sugar derivative.

11. The peritoneal dialysis fluid according to claim 10, containing from 35 to 45 g/l of said sugar derivative.

12. The peritoneal dialysis fluid according to claim 1, having an osmolality of 250 to 550 milliOsmols/l.

13. The peritoneal dialysis fluid according to claim 12, having an osmolality of 300 to 500 milliOsmols/l.

14. The peritoneal dialysis fluid according to claim 1, wherein $_{(\alpha g)}$ are (1→6) or (1→4) glycoside linkages.

15. The peritoneal dialysis fluid according to claim 1, wherein the sugar derivative is obtainable by chemical modification of an oligosaccharide containing 3 glucosyl units.

16. The peritoneal dialysis fluid according to claim 1, wherein said at least one sugar derivative is obtainable by a chemical modification of a mixture of one or more trisaccharides.

17. The peritoneal dialysis fluid according to claim 1, wherein said at least one sugar derivative is a mixture of hydrogenated trisaccharides, said hydrogenated trisaccharides having terminal sugar alcohol residues selected from the group consisting of sorbtiol, xylitol, ribitol and glycerol.

18. The peritoneal dialysis fluid according to claim 1, containing from 125 to 140 mEq/l of sodium, from 90 to 125 mEq/l of chloride, from 1 to 5 mEq/l of calcium, from 0.2 to 5 mEq/l of magnesium, and from 25 to 40 mEq/l of a buffering anion selected from the group consisting of lactate, pyruvate and bicarbonate.

19. The peritoneal dialysis fluid according to claim 1, having an osmolality of 280 to 455 milliOsmols per Liter.

20. The peritoneal dialysis fluid according to claim 1, comprising essential amino acids to increase the osmolality of the solution, to counterbalance amino acids loss or to provide the patient with protein nutrition.

21. A method of preparing the peritoneal dialysis fluid of claim 1, comprising adding sterile, pyrogen-free water to a composition comprising physiologically acceptable inorganic anions and cations and at least one sugar derivative as an osmotic agent, said physiologically acceptable inorganic anions and cations and said at least one sugar derivative being present in concentrations sufficient for the removal of water and solutes from a patient by peritoneal dialysis, wherein the sugar derivative is a compound of the formula

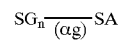

$$SG_n \overline{{}_{(\alpha g)}} SA$$

wherein each SG, which may be the same or different, represents a residue of a physiologically acceptable metabolizable sugar, SA represents a residue of a physiologically acceptable metabolizable sugar alcohol, n is 2, and $_{(\alpha g)}$ represents a glycoside linkage that is cleavable by an α-glycosidase enzyme; and wherein said composition is in dry form or in the form of an aqueous concentrate.

22. A method of performing peritoneal dialysis which comprises perfusing the peritoneal membrane of a patient with the peritoneal dialysis fluid of claim 1.

* * * * *